(12) United States Patent
Strauss et al.

(10) Patent No.: US 10,470,774 B2
(45) Date of Patent: Nov. 12, 2019

(54) EMBOLIC IMPLANT AND METHOD OF USE

(71) Applicant: Covidien LP, Mansfield, MA (US)

(72) Inventors: Brian Strauss, Irvine, CA (US); Jeffrey Valko, Irvine, CA (US); Jay Lenker, Laguna Beach, CA (US); Robert Pecor, Irvine, CA (US); Peter Barker, Irvine, CA (US); Maricruz Castaneda, Irvine, CA (US)

(73) Assignee: Covidien LP, Mansfield, MA (US)

( * ) Notice: Subject to any disclaimer, the term of this patent is extended or adjusted under 35 U.S.C. 154(b) by 100 days.

(21) Appl. No.: 15/072,873

(22) Filed: Mar. 17, 2016

(65) Prior Publication Data

US 2016/0192942 A1      Jul. 7, 2016

Related U.S. Application Data

(63) Continuation of application No. 14/171,088, filed on Feb. 3, 2014, now Pat. No. 9,301,827, which is a
(Continued)

(51) Int. Cl.
*A61B 17/12* (2006.01)
*A61L 31/02* (2006.01)
(Continued)

(52) U.S. Cl.
CPC .. *A61B 17/12172* (2013.01); *A61B 17/12031* (2013.01); *A61B 17/12036* (2013.01);
(Continued)

(58) Field of Classification Search
CPC ...... A61B 17/12031; A61B 2017/1209; A61B 17/12109; A61B 2017/12063; A61B 17/1204; A61B 17/12022; A61F 2/01; A61F 2002/011; A61F 2/013; A61F 2002/015; A61F 2002/016; A61F 2002/018
See application file for complete search history.

(56) References Cited

U.S. PATENT DOCUMENTS 5,683,411 A   11/1997   Kavteladze et al.
5,755,773 A   5/1998    Evans et al.
(Continued)

FOREIGN PATENT DOCUMENTS

EP    0793457 B1   10/2001
EP    0915685 B1   9/2004
(Continued)

OTHER PUBLICATIONS

International Search Report and Written Opinion from International Patent Application No. PCT/US2012/040012, dated Nov. 7, 2012, 16 pp.
(Continued)

*Primary Examiner* — Thomas M McEvoy
(74) *Attorney, Agent, or Firm* — Shumaker & Sieffert, P.A.

(57) ABSTRACT

A parent artery occlusion (PAO) device which provides for immediate occlusion of a cerebral artery to isolate a defect. The PAO device includes a self-expanding wire-frame prolate structure which is partially covered with an ePTFE membrane.

22 Claims, 20 Drawing Sheets

Related U.S. Application Data continuation of application No. 13/483,962, filed on May 30, 2012, now Pat. No. 8,641,777.

(60) Provisional application No. 61/493,108, filed on Jun. 3, 2011.

(51) Int. Cl.
| | |
|---|---|
| *A61L 31/10* | (2006.01) |
| *A61L 31/14* | (2006.01) |
| *A61F 2/91* | (2013.01) |
| *A61F 2/01* | (2006.01) |
| *A61F 2/82* | (2013.01) |
| *A61B 17/00* | (2006.01) |

(52) U.S. Cl.
CPC .. *A61B 17/12109* (2013.01); *A61B 17/12113* (2013.01); *A61B 17/12145* (2013.01); *A61B 17/12154* (2013.01); *A61F 2/01* (2013.01); *A61F 2/91* (2013.01); *A61L 31/022* (2013.01); *A61L 31/10* (2013.01); *A61L 31/146* (2013.01); *A61B 2017/00526* (2013.01); *A61B 2017/00539* (2013.01); *A61B 2017/00544* (2013.01); *A61B 2017/00557* (2013.01); *A61B 2017/00867* (2013.01); *A61B 2017/12054* (2013.01); *A61B 2017/12063* (2013.01); *A61B 2017/12068* (2013.01); *A61B 2017/12077* (2013.01); *A61B 2017/12081* (2013.01); *A61B 2017/12086* (2013.01); *A61B 2017/12095* (2013.01); *A61F 2002/823* (2013.01); *A61F 2220/0058* (2013.01); *A61F 2230/0071* (2013.01); *A61F 2230/0076* (2013.01); *A61L 2400/04* (2013.01); *A61L 2400/14* (2013.01); *A61L 2400/16* (2013.01); *A61L 2420/04* (2013.01); *A61L 2430/36* (2013.01)

(56) References Cited

U.S. PATENT DOCUMENTS

| | | | |
|---|---|---|---|
| 5,951,599 | A | 9/1999 | McCrory |
| 7,118,592 | B1 | 10/2006 | Dang et al. |
| 8,641,777 | B2 | 2/2014 | Strauss et al. |
| 9,301,827 | B2 | 4/2016 | Strauss et al. |
| 9,694,201 | B2 | 7/2017 | Strauss et al. |
| 2001/0001806 | A1 | 5/2001 | Turnlund et al. |
| 2003/0045898 | A1* | 3/2003 | Harrison ............ A61F 2/01 606/200 |
| 2003/0153943 | A1 | 8/2003 | Michael et al. |
| 2003/0163192 | A1 | 8/2003 | Wallace et al. |
| 2003/0229366 | A1 | 12/2003 | Reggie et al. |
| 2004/0068288 | A1* | 4/2004 | Palmer ............ A61B 17/221 606/200 |
| 2004/0091421 | A1 | 5/2004 | Aston et al. |
| 2005/0192620 | A1 | 9/2005 | Cully et al. |
| 2006/0015136 | A1* | 1/2006 | Besselink ........... A61F 2/013 606/200 |
| 2006/0241735 | A1 | 10/2006 | Tockman et al. |
| 2007/0135826 | A1 | 6/2007 | Zaver et al. |
| 2007/0299466 | A1* | 12/2007 | Sachar ............ A61F 2/013 606/200 |
| 2009/0099592 | A1 | 4/2009 | Buiser et al. |
| 2009/0105644 | A1 | 4/2009 | Leonard et al. |
| 2009/0287291 | A1 | 11/2009 | Becking et al. |
| 2011/0022149 | A1 | 1/2011 | Cox et al. |
| 2011/0054519 | A1 | 3/2011 | Neuss |
| 2011/0071624 | A1 | 3/2011 | Finch et al. |
| 2011/0160763 | A1 | 6/2011 | Ferrera et al. |

FOREIGN PATENT DOCUMENTS

| | | | |
|---|---|---|---|
| WO | 9726939 | A1 | 7/1997 |
| WO | 0072909 | A1 | 12/2000 |
| WO | 03063732 | A2 | 8/2003 |
| WO | 2010030993 | A1 | 3/2010 |
| WO | 2012166804 | A1 | 12/2012 |

OTHER PUBLICATIONS

Geyik et al., "Neuroapplication of Amplatzer Vascular Plug: A Novel Device for Parent Artery Occlusion," Interventional Neuroradiology, Journal of Neuroradiology, Springer, Nov. 29, 2007, 5 pp.
Supplementary Search Report from counterpart European Patent Application No. 12792999.0, dated Dec. 19, 2014, 6 pp.
Examination Report from counterpart European Application No. 12792999.0, dated Sep. 22, 2015, 5 pp.
First Examination Report from counterpart Australian Application No. 2012262331, dated Nov. 16, 2015, 2 pp.
Ross et al., "The Vascular Plug: A New Device for Parent Artery Occulsuion," AJNR AM J Neuroradiol, Feb. 2007, 2 pp.
Notification of Reason for Rejection, and translation thereof, from counterpart Japanese Application No. 2014-513667, dated Apr. 12, 2016, 5 pp.
Prosecution History from U.S. Appl. No. 13/483,962, dated Mar. 27, 2013 through Nov. 14, 2013, 44 pp.
Prosecution History from U.S. Appl. No. 14/171,088, dated May 18, 2015 through Dec. 30, 2015, 26 pp.
Extended Search Report from counterpart European Application No. 12792999.0, dated Dec. 3, 2014, 6 pp.
Examination Report No. 1 from counterpart Australian Application No. 2016202497, dated May 23, 2017, 2 pp.
Extended European Search Report from counterpart European Application No. 16185528.3, dated May 11, 2017, 10 pp.
Notice of Acceptance and allowed claims, from counterpart Australian Application No. 2016202497, dated Sep. 7, 2017, 8 pp.
International Preliminary Report on Patentability from International Application No. PCT/US2012/040012, dated Dec. 4, 2013, 6 pp.
Lopez-Benitez et al., "Protective Embolization of the Gastroduodenal Artery with a One-HydroCoil Technique in Radioembolization Procedures," Cardiovascular Interventional Radiology, vol. 36(1), Springer Online, Mar. 14, 2012, 6 pp.
Murthy et al., "Radioembolization of Yttrium-90 Microsperes for Hepatic Malignancy," Seminars Interventional Radiology, vol. 25(1), Mar. 2008, 10 pp.
U.S. Appl. No. 15/635,258, naming inventors Strauss et al., filed Jun. 28, 2017.
Examination Report from counterpart European Application No. 16185528.3, dated Oct. 16, 2018, 4 pp.
Office Action from counterpart Canadian Application No. 2,837,879 dated Jun. 7, 2018, 4 pp.
Response to Canadian Office Action dated Jun. 7, 2018 from counterpart Canadian application No. 2,837,879, filed Dec. 6, 2018, 41 pp.
Notice of Allowance from counterpart Canadian Application No. 2,837,879, dated Mar. 21, 2019, 1 pp.
Response to Examination Report dated Oct. 16, 2018, from counterpart European Application No. 16185528.3-1664, filed Apr. 12, 2019, 4 pp.

* cited by examiner

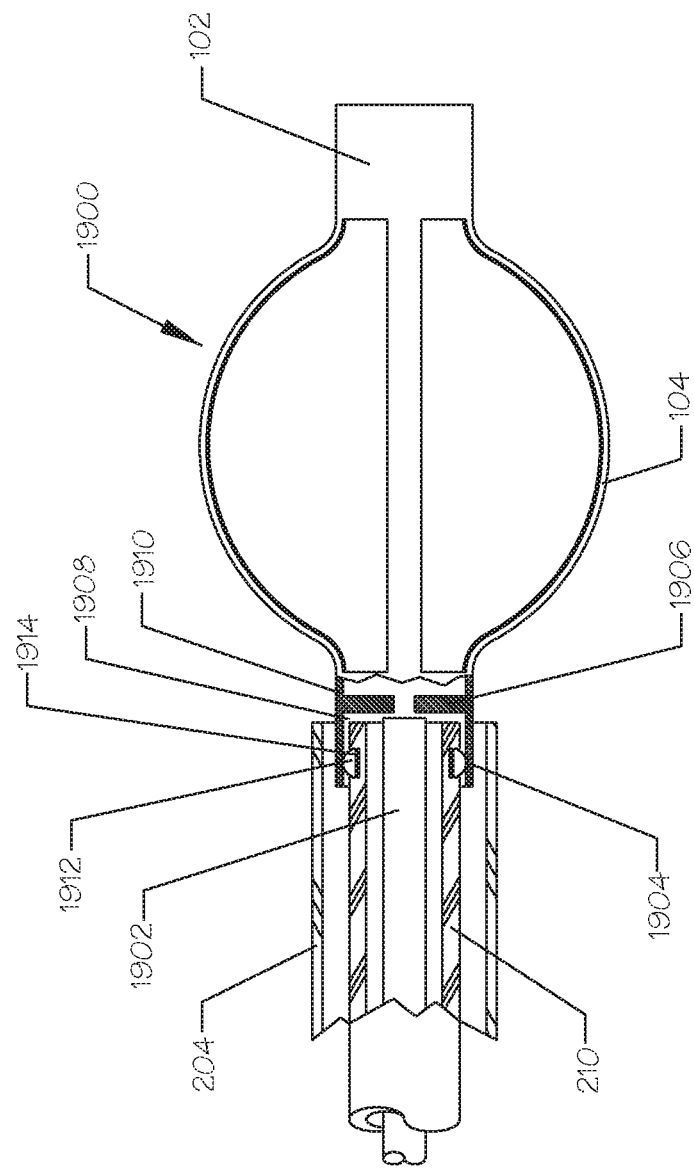

EMBOLIC IMPLANT AND METHOD OF USE

This application is a continuation of U.S. application Ser. No. 14/171,088, filed Feb. 3, 2014, which is a continuation of U.S. application Ser. No. 13/483,962, filed May 30, 2012, now U.S. Pat. No. 8,641,777 which claims priority to U.S. Provisional Application 61/493,108, filed Jun. 3, 2011. The entire content of each of these applications is incorporated herein by reference.

FIELD OF THE INVENTIONS

The inventions described below relate to the embolic devices for use in the neuro-vasculature (cerebral arteries and veins).

BACKGROUND OF THE INVENTIONS

The devices described below are intended for treatment of defects in the cerebral arteries and veins. Defects of the cerebral arteries include aneurysms, fusiform aneurysms, arteriovenous malformations, arteriovenous fistulas, cavernous fistulas and dissections and other hyper-vascular lesions (head and neck tumors, etc.). These defects cause of variety of symptoms, ranging from headache and vision loss to stroke and death. Preferably, these defects would be treated with devices and techniques that leave the associated parent artery or vein intact and patent so that it may continue to supply blood to regions of the brain which it naturally supplies. Such techniques include filling an aneurysm with occlusive polymers or occlusive coils, or inserting stents or covered stents, where feasible. In many cases, however, this is not advisable or possible because the artery vein segment in which the defect, or the defect itself, will not accommodate the devices, or because the patient's condition indicates that immediate cessation of blood flow is required.

The alternate, when parent artery preservation is not advisable, is parent artery occlusion, or PAO. Parent artery occlusion is accomplished by quickly and securely closing off a length of a blood vessel near the defect, and preferably results in immediate and complete blockage of blood flow to the defect, and permanent isolation of the blood vessel segment near the defect. Parent artery occlusion is sometimes referred to more broadly as parent vessel occlusion, to encompass occlusion of both arteries and veins. Several endovascular devices and techniques have been developed to accomplish parent artery occlusion. Detachable balloons have previously been proposed and used for parent artery occlusion, but were not successful because the balloons to often leaked and deflated, leading to major embolic complications. (Giant Intracranial Aneurysms at 257 (Awad, Issam and Barrow, Daniel, eds., Thieme/AANS 1st ed., 1995)). Occlusive coils have been used to pack fusiform aneurysms and cavernous fistulas, but this is extremely expensive (it may require dozens of coils) and does not result in immediate occlusion. Thus, trickling blood flow, which occurs for several minutes while the patient's blood is coagulating around the mass of coils, may lead to creation and migration of thrombus from the mass of coils. Vascular plugs have been used to accomplish parent artery occlusion. Currently available plugs, such as the Amplatzer vascular plug, are used off-label in the neuro-vasculature, and are difficult to deploy. Ross, et al., The Vascular Plug: A New Device for Parent Artery Occlusion, 28 AJNR Am J Neuroradiology 385 (February 2007). Also, the open-mesh construction of these vascular plugs may result in dislodgement of thrombus as it is forming on the plug, leading to embolization downstream of the occluded artery.

SUMMARY OF THE INVENTIONS

The devices and methods described below provide for expeditious embolization of arteries of the neuro-vasculature with an embolic implant, and suitable for use as a parent artery occlusion device within a cerebral artery (or within a cerebral vein). The devices may also be deposited in aneurysms. The embolic implant includes a self-expanding cage-like wire-frame structure, which may be elongate or spherical, or oblate or prolate spheroid, which is covered with a polymer membrane. The embolic device is releasably attached to the delivery catheter with mechanical attachment means such as detents, electrolytic detachment or other suitable detachment means. Upon release from the delivery catheter, the embolic device expands toward its unrestrained shape, to the extent allowed by the surrounding cerebral artery. Expansion of the cage like structure, and concurrent expansion of the membrane, results in immediate occlusion of the cerebral artery. In recent comparative studies, the embolic implant stopped blood flow in an artery in about 15 seconds, as compared to the Amplatzer vascular plug, which took 3 minutes to stop blood flow.

Additionally these devices are used to perform pre-operative de-vascularization and test occlusions. Additional embolic implants are also disclosed, which include cage-like bodies formed with struts and restraining bands. Though proposes for use within the cerebral vasculature, the devices may also be used to treat defects blood vessels throughout the body.

BRIEF DESCRIPTION OF THE DRAWINGS

FIG. 32 illustrates a side view of an embolic implant, in partial breakaway view, showing a pusher system to detach and deploy the implant.

DETAILED DESCRIPTION OF THE INVENTIONS

Figure 1:
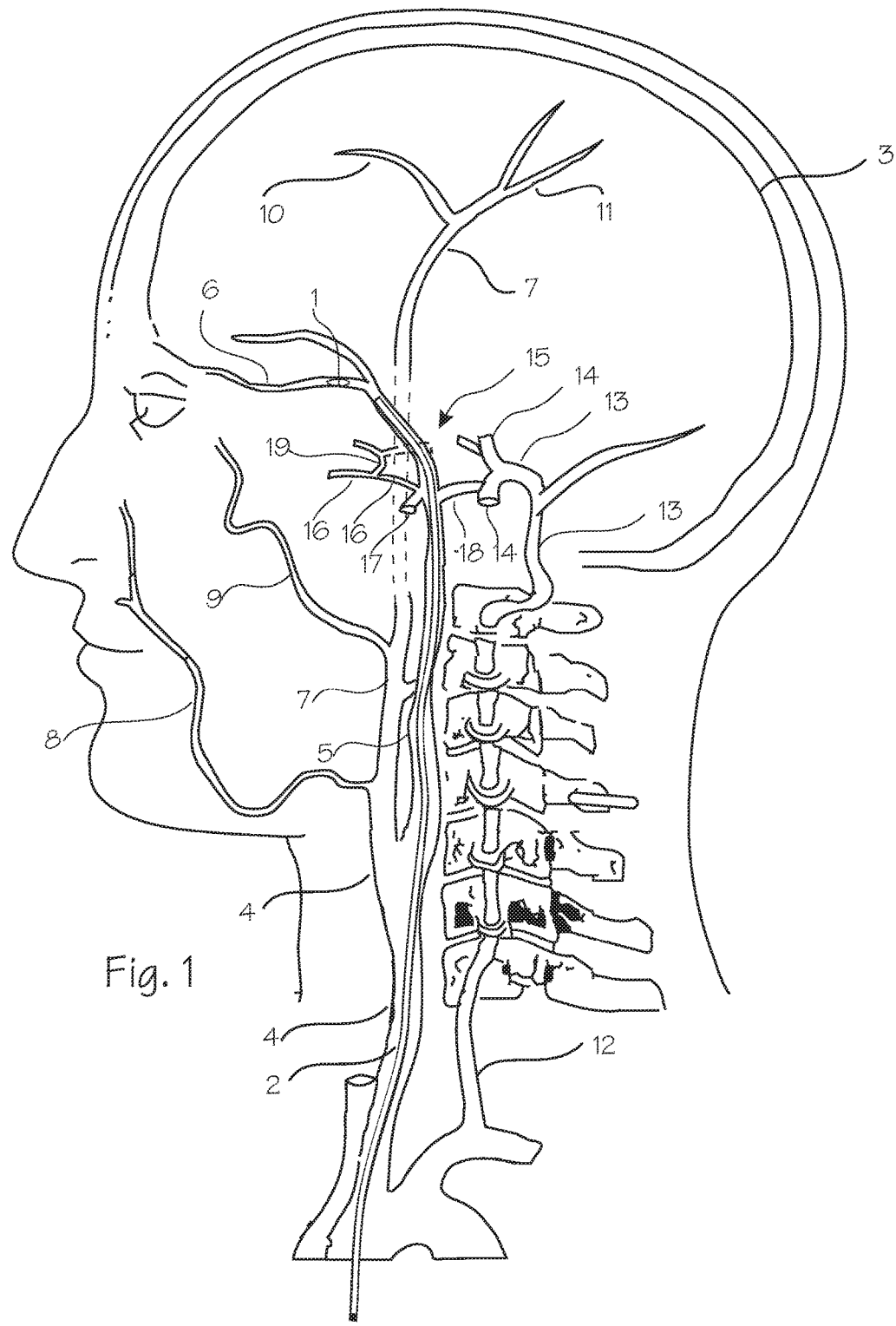
FIG. 1 is a schematic diagram of the vasculature of the brain showing a typical placement of an intra-cranial embolic device.
Figure 2:
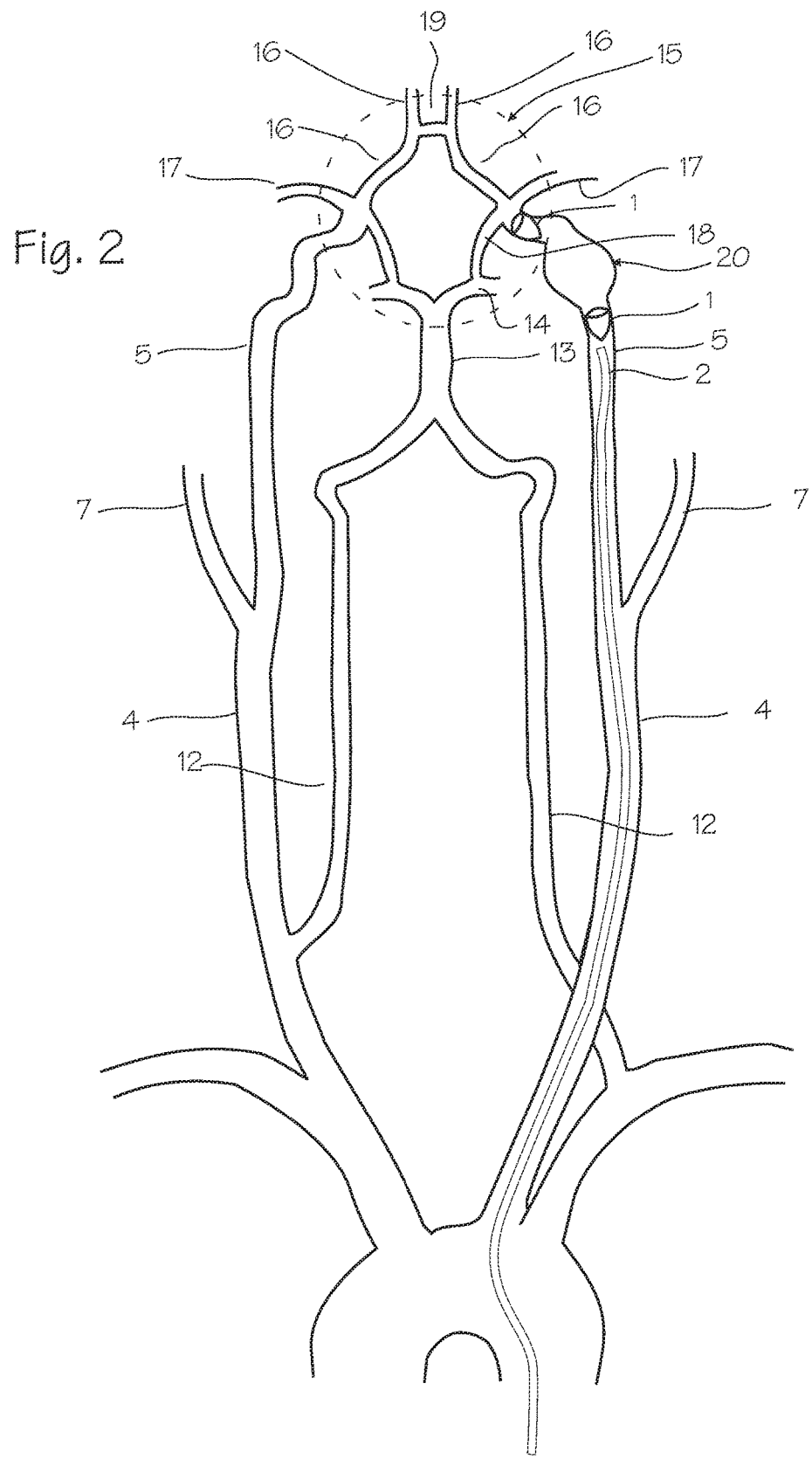
FIG. 2 is schematic diagram of the vascular of the brain illustrating the circle of Willis and arteries supplying the circle of Willis.

FIGS. 1 and 2 show the vasculature of the brain in sufficient detail to illustrate the use of the embolic implants shown in the following illustrations. The embolic implant 1 is shown in an exemplary placement. The embolic implant is delivered to this site of a vascular defect with the delivery catheter 2. The neuro-vasculature, which is the intended environment of use for the embolic implant, supplies the brain 3 with blood through the carotid and the vertebral arteries on each side of the neck. The important arteries include the common carotid artery 4 in the neck, which will be the most common access pathway for the embolic implants, and the internal carotid artery 5 which supplies the ophthalmic artery 6. The external carotid 7 supplies the maxillary artery 8, the middle meningeal artery 9, and the superficial temporal arteries 10 (frontal) and 11 (parietal). The vertebral artery 12 supplies the basilar artery 13 and the cerebral arteries including the posterior cerebral artery 14 and the circle of Willis indicated generally at 15. The siphon 12a of the vertebral artery appears in the intra-cranial vasculature on the vertebral approach to the Circle of Willis. Also supplied by the internal carotid artery are the anterior cerebral artery 16 and the middle cerebral artery 17, as well as the circle of Willis, including the posterior communicating artery 18 and the anterior communicating artery 19. The siphon 5a of the internal carotid artery 5 appears in the intra-cranial vasculature on the carotid approach into the Circle of Willis. These arteries typically have an internal diameter of about 1 mm to 5 mm, most commonly from 2-4 mm. The methods and devices described herein allow access to these arteries and placement of a stent in these arteries. In FIG. 1, the insertion catheter and an embolic implant 1 are shown threaded through the common carotid artery 4 and the internal carotid artery 5, with the embolic implant disposed within the anterior cerebral artery 16.

FIG. 2 shows the same blood vessels in a schematic view that better illustrates the Circle of Willis and the arteries which supply this important anatomic feature. The Circle of Willis 15 is a ring of arteries connecting the internal carotid arteries and the basilar artery (and hence the left and right vertebral arteries) to the anterior cerebral arteries 16, middle cerebral arteries 17 and posterior cerebral arteries 14. The system provides a redundant supply of blood to the cerebral arteries. The carotid siphon 5a, which forms an integral part of the internal carotid artery 5, is more clearly visible in this view. Aneurysms, fistulas, AVM's and tumors occurring inside the brain, in the intracranial portion of the carotid arteries, vertebral arteries (and the portions of those arteries distal to the siphons) and basilar artery, in the circle of Willis or even deeper within the brain may be treated with the embolic implants and delivery systems described below. FIG. 2 shows an exemplary use in which a delivery catheter 2 is inserted through the aorta into the common carotid to the internal carotid to treat an vascular defect 20 (a fusiform aneurysm, in this case) with a embolic implants. One implant is deposited distal to the defect to block retrograde blood flow coming from the Circle of Willis, and one implant is deposited proximal to the defect to block normal blood flow from the internal carotid artery. Sacrifice of this parent artery isolates the defect, but the neuro-vasculature on this side of the brain will be supplied the redundant route through the Circle of Willis. It should be appreciated, however, that any thrombus thrown off from the embolic implant due to delay in stopping normally directed blood flow might result in blockage of downstream arteries.

Figure 3:
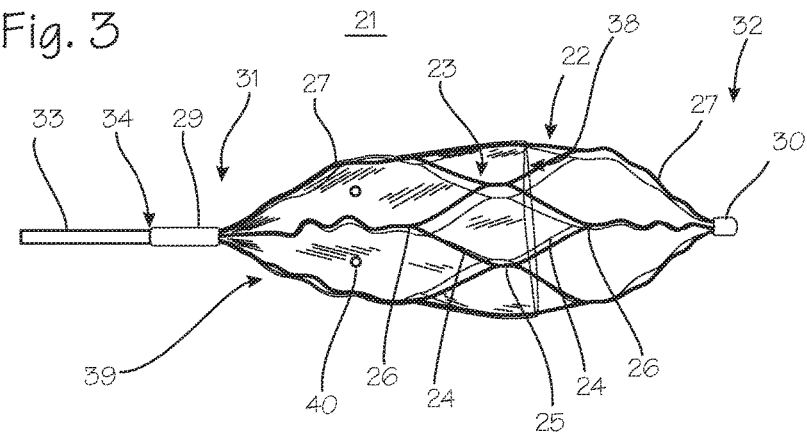
FIG. 3 illustrates an embolic implant with a oblong prolate wire-frame structure which is partially covered with a membrane.

FIG. 3 illustrates an embolic implant, or parent artery occlusion device, suitable for use in the neuro-vasculature of a patient. The embolic implant 21 is wire-frame structure with an overall tubular shape, with struts converging to the longitudinal center (the long axis) of the device where they are bound together with rings. The wire frame structure is partially covered with a membrane. The wire-frame structure is formed by laser-cutting a nitinol tube. The resultant segments of the wire-frame structure include a first zig-zag segment 22 and a second zig-zag segment 23, with V-shaped elements 24 joined at the "open" end of the V, through small longitudinal struts 25. These struts are longitudinally offset from each other, so that the embolic implant can be compressed into a small diameter configuration in which the struts and the junctions between the zig-zag segments can be compressed to smaller diameter than would be possible if the struts were longitudinally aligned. The struts can be compressed into a diameter smaller than the original tube from which the device is cut. Each zig-zag segment is characterized by vertices 26 of each V-shaped element which point longitudinally away from the longitudinal center of the device. From the vertices of the V-shaped elements, end struts 27 extend longitudinally away from the longitudinal center of the device, and curve inwardly toward the radial center of the device. The proximal serpentine struts continue into a segment of straight struts 28 (see FIG. 4). The distal serpentine struts continue into a segment of straight struts 37 (see FIG. 4). The ends of the end struts furthest from the longitudinal center are secured in small rings 29 and 30. (The rings are made of a radiopaque material, such as gold, platinum alloys, etc., to help facilitate placement of the embolic implant under fluoroscopic guidance.) The device can be characterized by a proximal end 31 and a distal end 32, defined in reference to the delivery catheter used to implant the device, and the pathway along which the implant is navigated to reach the implant site. At the proximal end, the wire frame structure is joined to a delivery rod 33 through an electrolytic detachment joint 34. The electrolytic detachment joint is heated to break the joint by applying current from a power source at the proximal end of delivery rod. (The electrolytic detachment joint is broken when low current is applied to it to elicit an electro-chemical reaction.) (Also, any of the detachment means described below may be used to hold the embolic implant during delivery and detach it from the delivery rod.)

Figure 4:
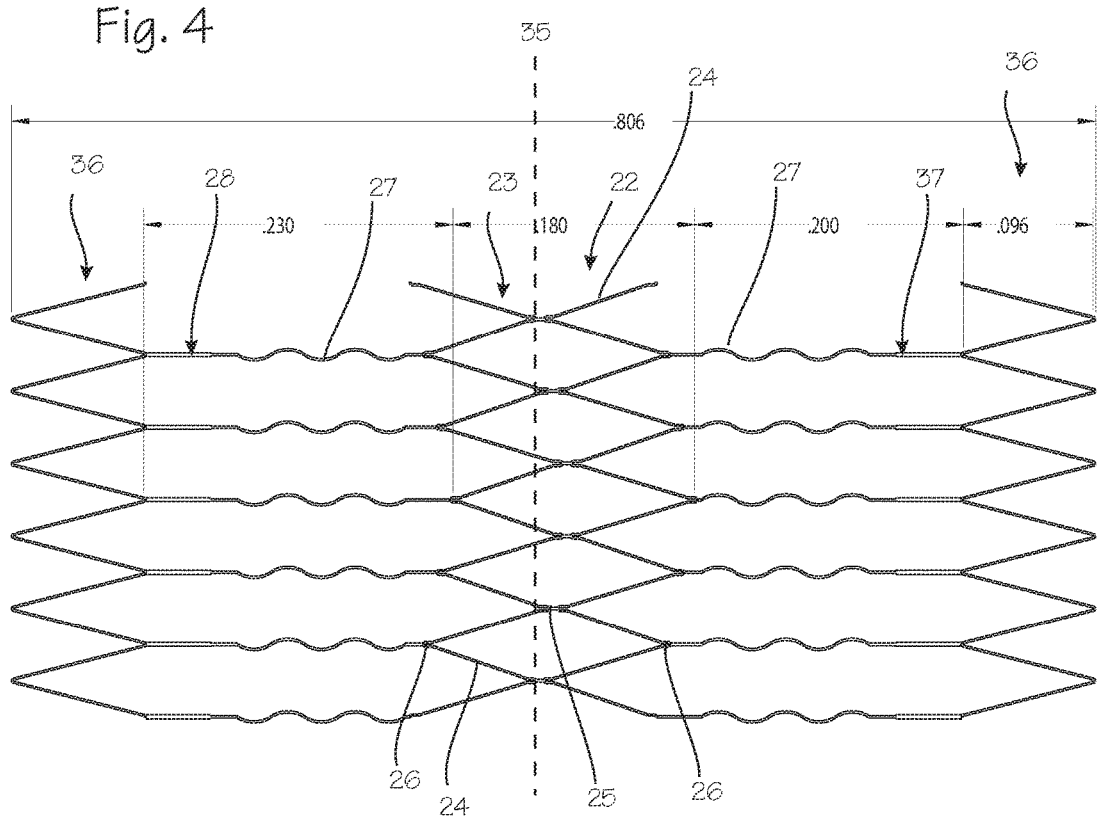
FIG. 4 illustrates the several segments of the parent artery occlusion device.

FIG. 4 illustrates the wire frame structure, as if unrolled, to illustrate its several segments. The first and second zig-zag segments 22 and 23 are connected through small central struts 25. The circumferential line marked as item 35 is shown to illustrate the longitudinal displacement of the struts relative to each other. Because the struts and the V vertices are not aligned along the same circumferential line, the implant can be compacted without being limited by interfering contact of the struts. The serpentine struts extending longitudinally from the zig-zag segments connect to scrap zig-zag segments 36. These segments are formed during the laser cutting process, and are used to facilitate gathering of the serpentine struts into the rings at either end of the device. After the serpentine struts are secured in the rings, these portions are removed and discarded. As indicated in FIG. 4, the central zig-zag segments are joined together to form several diamond shaped cells with longitudinally displaced vertices, referring both to the longitudinally pointing vertices and the circumferential vertices. The combined zig-zag segments span 0.180" along the longitudinal axis of the device. The serpentine struts span 0.230".

The wire-frame structure is preferably made of superelastic alloy, formulated to be superelastic at body temperature, such that the implant is self-expanding upon release from its delivery catheter. It may also be made of resilient metals or polymers, or shape memory alloy or shape memory polymers. The zig-zag segments are illustrated with sharply defined V-shaped elements, which assists in compacting the device. The V-shaped elements can be replaced with U-shaped elements, or sinusoidally curved elements, to create a serpentine segments which are joined together and the serpentine struts joined to the bottom of the U-shaped elements.

Referring again to FIG. 3, the wire-frame structure of the embolic implant is covered with a membrane 38. The membrane 38 covers the proximal end of the embolic implant, from the ring 30 to the longitudinal center of the implant, and, as illustrated, extending over both zig-zag segments. The membrane is made of ePTFE and is glued to the metal struts of the wire-frame structure with suitable adhesive. This membrane is impermeable to blood on the proximal facing surface 39, and may also be impermeable on the circumferential surface which covers the center of the device. However, as illustrated, the circumferential surface of the membrane, which will be pressed against the wall of the vessel at the implant site, may be perforated with perforations or "weep holes" 40. These perforations will facilitate purging the device of air just prior to implantation. Weep holes may also be provided in the proximal-facing surface of the membrane, if it beneficial to permit some small seepage of blood past the membrane.

The membrane, as illustrated, is made of two 0.0003" (0.00762 mm) thick sheets of ePTFE with a layer of adhesive, such as Bacon Adhesive 430 or 431, sandwiched between the two ePTFE sheets such that the ePTFE is impregnated with the adhesive. The membrane material is prepared by applying the adhesive to one sheet, and scraping or pressing the adhesive away, leaving the sheet wetted with a thin layer of adhesive on the surface of the sheet and leaving adhesive impressed into the pores of the ePTFE. The second sheet is then disposed over the wetted surface, that this assembly is then scraped and pressed to flatten the assembly. The result is a sheet of ePTFE which can be glued to the metal struts of the wire-frame structure, despite the normal resistance of ePTFE to adhesion. Tantalum powder may be mixed into the adhesive to provide some degree of radiopacity to the completed membrane. The sheet is then formed into the roughly conical shape shown, stretched over a conical mandrel, and heated then peeled off the mandrel. It is then glued or otherwise affixed to the expanded wire-frame structure. The membrane can also be formed of a single layer of ePTFE which is stretched and heat-formed to match the outer circumference of the expanded wire-frame structure.

The embolic implant may be fashioned so that it opens to a fully expanded, unrestrained diameter of 5 mm at its center, but can be compacted to a diameter of less than 1 mm, and preferably to a diameter of about 0.5 mm to fit in a delivery catheter with an internal diameter of 0.021" (0.5334 mm) or less and outer diameter of 0.0.039" (1 mm) (3 F) or less. This permits far greater access than a comparable Amplatzer™ PAO device. An Amplatzer™ at 6 mm in expanded diameter when fully compacted for delivery, requires a 5 to 6 F (1.7 mm to 2 mm) delivery catheter with an internal diameter of 0.054" to 0.072" (1.37 mm to 1.83 mm).

The embolic implant can be coated to enhance thrombogenicity or space-filling characteristics within its structure. Coatings can include hydrophilic hydrogel or expandable foam which is applied to the implant 100 and dried prior to use. Upon exposure to blood or other liquid, the hydrogel or foam absorbs water and swells in volume. Such volume swelling can increase the hydrogel or foam layer thickness up to ten times, or more. The hydrophilic hydrogel can comprise fibrin glue, prothrombin, or other blood clotting substance. Thrombogenic (blood clotting) chemicals can be applied to the embolic implant with or without the hydrogel.

In use, a vascular surgeon (typically an interventional radiologist) inserts the embolic implant, packed in a delivery catheter, to a segment of the cerebral artery (or vein) with a defect. This will typically be accomplished through a guide catheter, which the surgeon will insert prior to inserting the delivery catheter. After confirming the location of the device (under fluoroscopy), the surgeon withdraws the delivery catheter to expose and release the embolic implant. The embolic implant may be drawn back into the delivery catheter and repositioned if necessary (via the delivery wire). When the embolic implant is properly positioned and deployed from the delivery catheter, the surgeon operates a small power supply to deliver electric current through a conductor running from the detachment joint to the power supply (the pushrod may serve as the conductor) to melt or electrolytically sever the joint and detach the embolic implant from the pushrod. A single implant can be used to isolate blood vessels that are not exposed to redundant blood supply or retrograde flow. For blood vessels subject to redundant blood supply, such as the internal carotid arteries, the surgeon will place a first implant distal to the defect to prevent retrograde flow and a second implant to prevent antegrade flow. Additionally, the embolic implant can be used to temporarily occlude a blood vessel, and the entire system used as a drug or other therapeutic agent delivery device, where the implant is delivered out the end of the catheter and expanded to occlude the blood vessel, after which drugs or therapeutic agents are delivered from the delivery catheter, the guide catheter or an additional catheter, just proximal to the embolic device, allowing the therapeutic agents to be released to the vascular target more precisely. In this case, the implant maintained securely on the delivery rod, and is not detached, but is removed from the vasculature after the delivery of the agents.

In the same manner, the system can be used for test occlusion. This is a diagnostic technique in which the surgeon temporarily deploys the embolic device, without detaching it from the delivery rod, to occlude blood flow to a suspected segment in the cerebral vasculature to test the segment and ensure that any defects in that segment are the cause of symptoms observed in the patient. If the observed symptoms are ameliorated by the test occlusion, the surgeon may, depending on defect shape, size and location, remove the embolic implant from the suspected segment and withdraw the delivery catheter from the cerebral vasculature, and then proceed to treat the defect with coils, stents, embolic substances, etc. to preserve the patency of the blood vessel that has been tested. If, on the other hand, the defect shape, size and location are such that the segment should be sacrificed and occluded, the surgeon may detach the embolic implant from the delivery rod to occlude the segment. Because the embolic implant of FIG. 3 and the remaining Figures provides for immediate but easily reversible occlusion, it is uniquely suited for test occlusion. The system can also be used for pre-operative de-vascularization, as an adjunct to surgical resection of arterio-venous malformations (AVM's) and tumors. In a method, a surgeon, prior to surgically resecting an AVM or tumor in the brain, implants one or more embolic devices in arteries supplying blood to the AVM or tumor, and may also implant one or more embolic devices in veins returning blood from the AVM or tumor, and thereafter resect the AVM or tumor in an open surgery. With this method, bleeding can be greatly diminished when the AVM or tumor is cut from the body. Because the embolic implant of FIG. 3 and the remaining Figures provides for immediate but easily reversible occlusion, it is uniquely suited for pre-operative de-vascularization.

Figure 5:
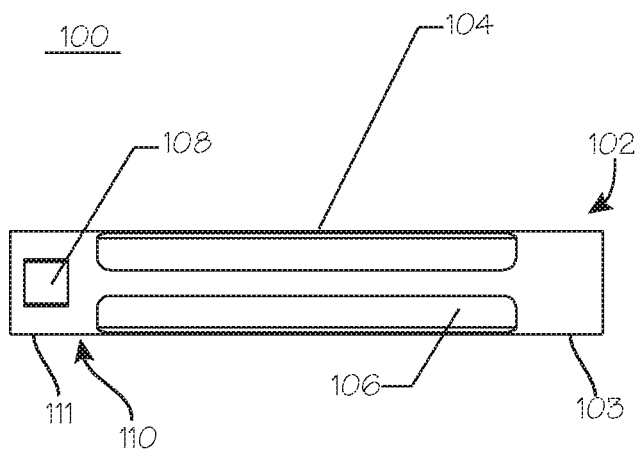
FIG. 5 illustrates a side view of an embolic implant, comprising a plurality of longitudinal struts, in its unexpanded state.

The embolic implant can be configured in various embodiments. FIG. 5 illustrates a side view of an embolic implant 100, in its first, small diameter, unexpanded state, comprising a proximal end 110, a distal end 102, a plurality of longitudinally oriented struts 104, and a plurality of longitudinally oriented slots. The plurality of longitudinal struts 104 are affixed, or integral to, to the proximal band 111 and to the distal band 103. The plurality of longitudinal slots 106 can be fenestrations in the implant such that the remaining structure comprises the plurality of struts 104. The locking feature 108 can be affixed, or integral to, the proximal end 110, the distal end 102, or both. The locking feature 108 can comprise a fenestration in the proximal end 110, as illustrated, or it can comprise a structure radially projecting either outward or inward from the axis of the implant 100. The locking features 108 can comprise any shape such as circular, rectangular (as illustrated), linear, circumferential, or the like.

Figure 6:
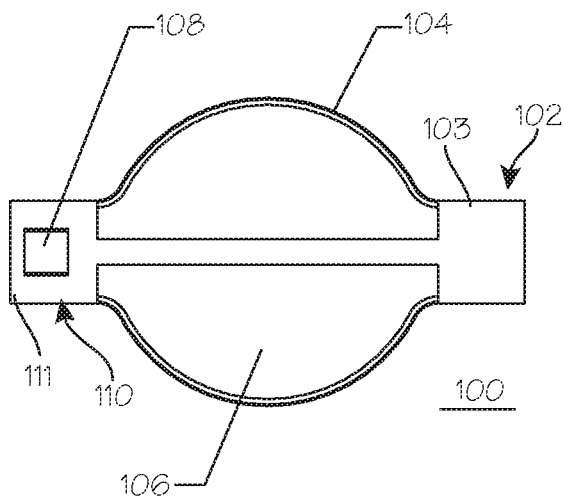
FIG. 6 illustrates a side view of an embolic implant of FIG. 5, which has been radially expanded by foreshortening the distance between its two ends.

FIG. 6 illustrates a side view of the implant 100 with its struts 104 expanded to their second, enlarged configuration. The implant 100 comprises the proximal band 111, the distal band 103, the plurality of struts 104, the plurality of slots 106, and the latch element 108. The struts 104 have expanded to form an arcuate shape and then curving back into alignment with the longitudinal axis of the implant 100 at the point where they are affixed to the proximal band 111 and the distal band 103. There are four struts 104 and four slots 106. The strut 104 in the background is hidden by the strut 104 in front. The top and bottom struts 104 are visible. The diameter of the expanded implant 100, measured at the center of the struts 104 is approximately 3 mm. More or less expansion can be achieved depending on the length of the struts 104 and the amount of strain applied to the struts 104. It is beneficial to keep the amount of strain within the linear range for the material used in fabricating the struts 104. The slots 106 become distorted and enlarge significantly for the expanded configuration of the implant 100. By increasing the number of struts 104 and slots 106, greater fill can be achieved. Greater numbers of struts 104 can be achieved by making the struts 104 narrower, the slots 106 narrower, or both. It is possible to achieve up to eight, ten, or even twelve struts in a 1 mm diameter unexpanded implant 100. Even higher numbers of struts 104 are achievable if the struts 104 are fabricated from small diameter, round, or rectangular, wire affixed to the ends 110 and 102.

Figure 7:
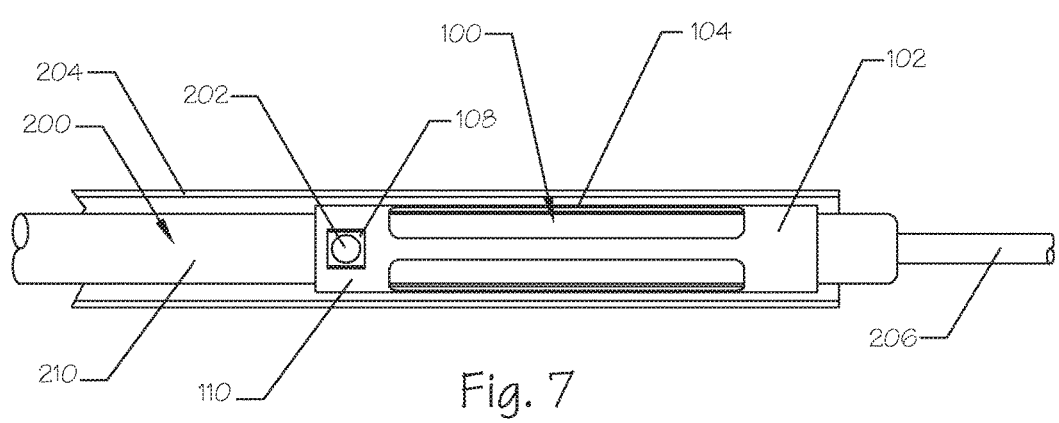
FIG. 7 illustrates a side view of the unexpanded embolic implant of FIG. 6 releasably affixed to the distal end of a delivery catheter and further inserted through the lumen of a guide catheter along with a guidewire.

FIG. 7 illustrates a side view of the implant 100 loaded onto a delivery catheter tube 210 and slidably movable within a guide catheter tube 204, the latter of which is shown in cross-section. The delivery catheter tube 210 is comprised by a delivery catheter 200 and is slidably disposed over a guidewire 206 which is routed through a lumen of the catheter tube 210. The implant 100 comprises the plurality of struts 104, the distal end 102, the proximal end 110, and the latch feature 108. The delivery catheter 200 further comprises a releasable lock 202.

Figure 8:
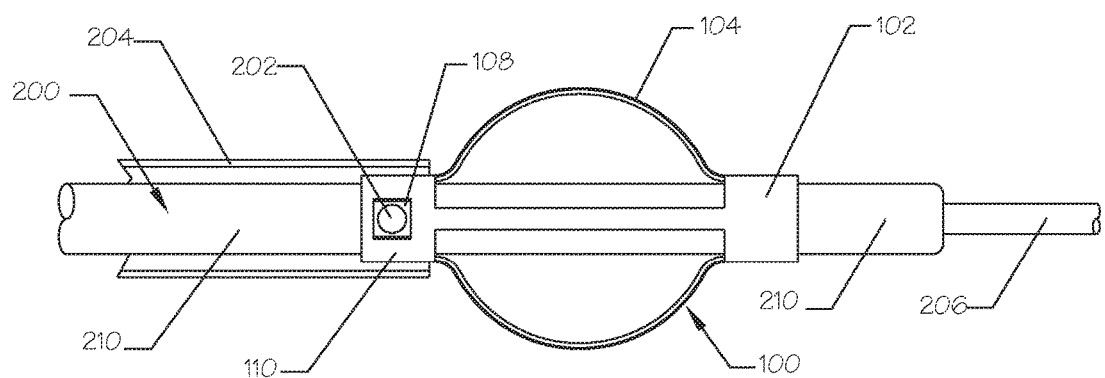
FIG. 8 illustrates a side view of the embolic implant of FIG. 6 releasably affixed to the distal end of the delivery catheter and advanced out the distal end of the guide catheter along with the guidewire, allowing the implant to expand radially.

Referring to FIGS. 7 and 8, the catheter tube 210 is slidably movable within the central lumen 112 of the implant 100. The guidewire 206 is slidably movable within a lumen (not shown) of the catheter tube 210 and projects beyond the distal end of the catheter tube 210. The locking mechanism 202, affixed to the catheter tube 210 projects outward through the latch feature 108 comprised by the proximal end 110 of the implant 100. The implant struts 104 are spring metal such as superelastic nitinol and are biased outward to form a curve or arc when unconstrained. The struts 104, however, are constrained by the wall of the guide catheter 204 through which the implant 100 is being advanced. Thus the struts 104 are compressed or collapsed into their first, low profile configuration or shape.

FIG. 8 illustrates a side view of the implant 100 having been advanced out the distal end of the guide catheter tube 204. The implant 100 comprises the struts 104, the distal end 102, the proximal end 110, and the latch feature 108. The delivery catheter 200 comprises the delivery catheter tube 210 and the locking mechanism 202. The guidewire 206 is disposed within the lumen of the catheter tube 210 and projects out the distal end thereof. The struts 104 have expanded radially (outwardly in relation to the longitudinal axis of the implant 100). The expanded struts 104 form an arc shape but the shape could be triangular, rectangular, trapezoidal, or the like. The struts, possess spring-characteristics and resiliently expand once the constraint of the guide catheter tube 204 has been removed. The proximal end 110 of the implant 100 is fixed relative to the catheter tube 210 by the locking mechanism 202 still being engaged with the latch feature 108. The distal end 102 of the implant 100 slides longitudinally proximally over the catheter tubing 210 and is now further from the distal end of the catheter tubing 210 than when the implant 100 is in the unexpanded state, since the distal end 102 moves closer to the proximal end 110 to facilitate the lateral expansion of the struts 104. The implant 100 remains affixed to the delivery catheter 200 until a user operated a release mechanism from the proximal end of the delivery catheter 200.

Figure 9:
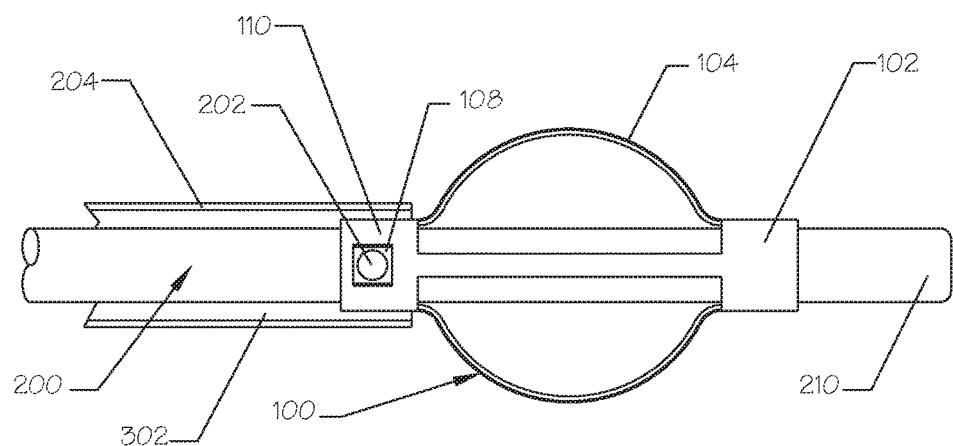
FIG. 9 illustrates the expanded embolic implant of FIG. 2B wherein the guidewire has been withdrawn so that the distal end of the guidewire is proximal to the proximal end of the implant such that the implant is released from the delivery catheter.

FIG. 9 illustrates a side view of the implant 100, the delivery catheter 200, and the guide catheter tube 204. The delivery catheter 200 comprises the delivery catheter tube and the locking mechanism 202. The implant 100 comprises the plurality of struts 104, the distal end 102, the proximal end 110, and the latch feature 108. The guide catheter tube 204 comprises a central lumen 302.

Referring to FIGS. 9 and 8, the guidewire 206 has been removed from the lumen of the delivery catheter tube 210. Removal of the guidewire has caused the locking mechanism 202 to retract radially inward and disengage with the latching feature 108 on the implant 100. The proximal end 110 of the implant 100 is still positioned within the lumen 302 of the guide catheter tubing 204.

Figure 10:
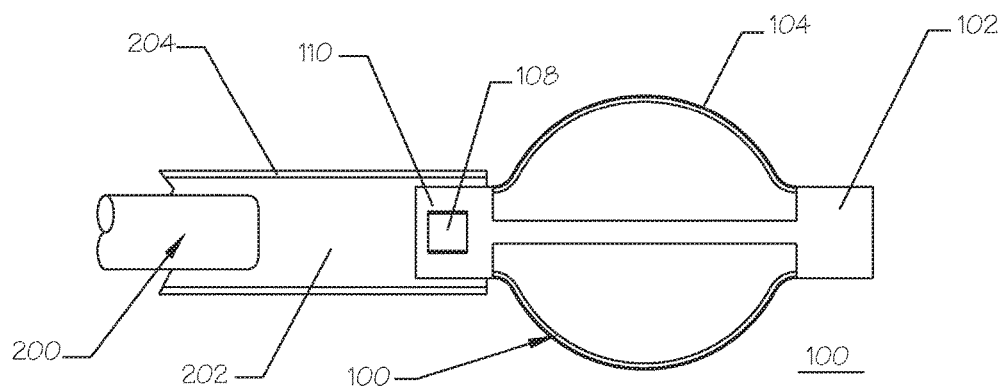
FIG. 10 illustrates the embolic implant of FIG. 9 wherein the delivery catheter has been withdrawn proximally away from the released embolic implant.

FIG. 10 illustrates a side view of the implant 100, the delivery catheter 200 and the guide catheter tube 204. The guide catheter tube 204 comprises the central lumen 302. The implant 100 comprises the distal end 102, the plurality of struts 104, the proximal end 110, and the latch feature 108. The delivery catheter 200 has been withdrawn proximally out of the lumen of the implant 100 and is being withdrawn out of the guide catheter tube 204. Since the lock 202 on the delivery catheter 200 was released, it no longer prevents relative longitudinal movement between the catheter tube 210 and the implant 100. The proximal end 110 of the implant remains within the lumen 302 of the guide catheter tubing 204. However, proximal withdrawal of the guide catheter tube 204 will completely disengage the implant 100 from the guide catheter tube 204 leaving the implant within the vessel to embolize, thrombose, and occlude the vessel.

Figure 11:
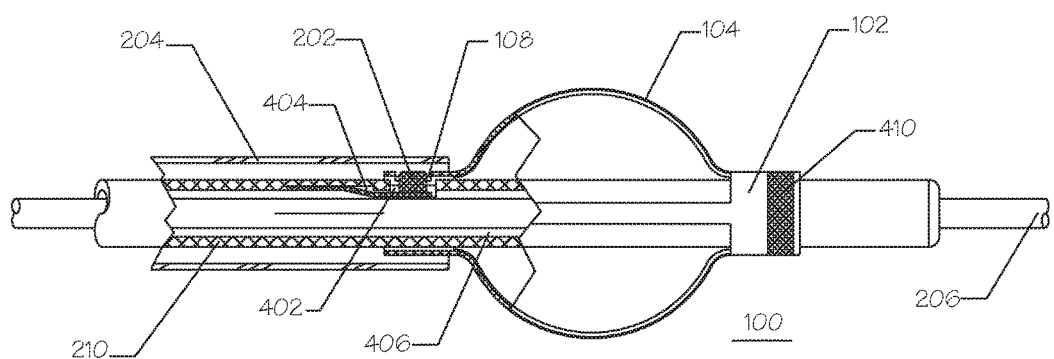
FIG. 11 illustrates the embolic implant of FIG. 7, rotated 90 degrees, in a side partial breakaway view such that the releasable locking mechanism is illustrated.

FIG. 11 illustrates a side partial breakaway view of the implant 100, the delivery catheter tube 210, the guide catheter tube 204, and the guidewire 206 of FIG. 8 but rotated 90 degrees out of the plane of the page to permit a side view of the workings of the releasable lock 202 and the latch feature 108. The delivery catheter tube 210 further comprises the releasable lock 202, the lock spring 404, and the lock opening 402. The implant 100 further comprises the distal end 102, the plurality of struts 104, the proximal end 110, a radiopaque marker 410, and the latch feature 108. The guidewire 206 extends through a lumen 406 of the delivery catheter tube 210. The guidewire 206 fills a substantial portion of the catheter lumen 406 and forces the lock spring to become compressed radially outward forcing the releasable lock 202 to be forced outward through the latch opening 404 in the catheter tube 204. The releasable lock 202 is forced outward and engages within the latch feature 108 on the implant 100 preventing the implant 100 from moving either proximally or distally relative to the catheter tube 210. The implant 100 is constrained and cannot move radially, in a substantial, or functionally meaningful, amount relative to the delivery catheter tube 210 since it is slidably movably disposed over the delivery catheter tube 210. The latch feature 108 can be located on the proximal end 110, the distal end 102, or both, of the implant 100.

The cross-section of the catheter wall is illustrated with a cross-hatch and can comprise a braid or coil reinforcement of metal, such as but not limited to, stainless steel, titanium, nitinol, or the like, or polymer, such as polyethylene naphthalate (PEN), PET or the like, embedded within a polymeric surround. The releasable lock 202 is affixed to a first end of the lock spring 404. The lock spring 404, which is illustrated as a cantilever spring, is affixed at a second end to the catheter tubing 210. The lock spring 404 can be fabricated from metals such as, but not limited to, nitinol, stainless steel, titanium, cobalt nickel alloy, or the like. The lock spring 404 can also be fabricated from polymers such as, but not limited to, PEEK, PEN, PET, polycarbonate, and the like. The lock spring 404 can be affixed to the catheter tube 210 using adhesives, fasteners, heat welding, ultrasonic welding, and the like.

Figure 12:
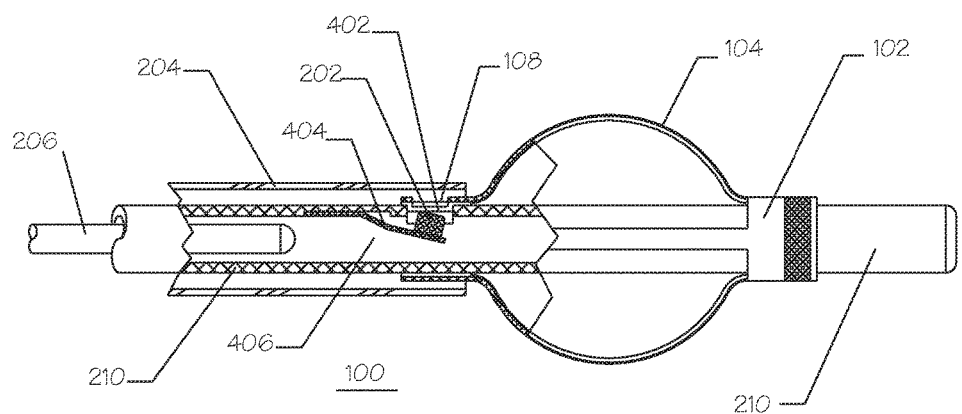
FIG. 12 illustrates the embolic implant of FIG. 11 in partial breakaway view with the guidewire having been withdrawn and the locking mechanism released from the embolic implant.

FIG. 12 illustrates a side view of the implant 100 and its delivery system of FIG. 11 but with the guidewire 206 having been withdrawn proximally and removed from inside the implant 100. The lock spring 404 has returned to its unrestrained position and has withdrawn the releasable lock 202 to a position inside the lock opening 402 such that the releasable lock 202 no longer engages with the latch feature 108 on the implant 100. Thus, the implant 100 is now free to move longitudinally along the delivery catheter tubing 210.

The releasable lock 202 may also be operated by a separate linkage (not shown) disposed through the central lumen coaxially around the guidewire or through a separate lumen. The linkage can be configured to pull, push, or rotate such that the releasable lock 202 can be moved radially inward and outward. The rotational linkage can turn a jackscrew or worm gear to move the lock 202 inward and outward. An electrically powered actuator (not shown) can be used to lock and unlock the catheter tubing 210 from the implant 100. The implant 100 can be released from the catheter tubing 210 by means of a fluidic system operably configured to provide either positive or negative pressure to drive the implant off of the catheter or disengage the releasable lock 202. Ohmic or resistive heating can be used to move a shape memory or heat-reactive material to force disengagement between the implant 100 and the catheter tubing 210.

Figure 13:
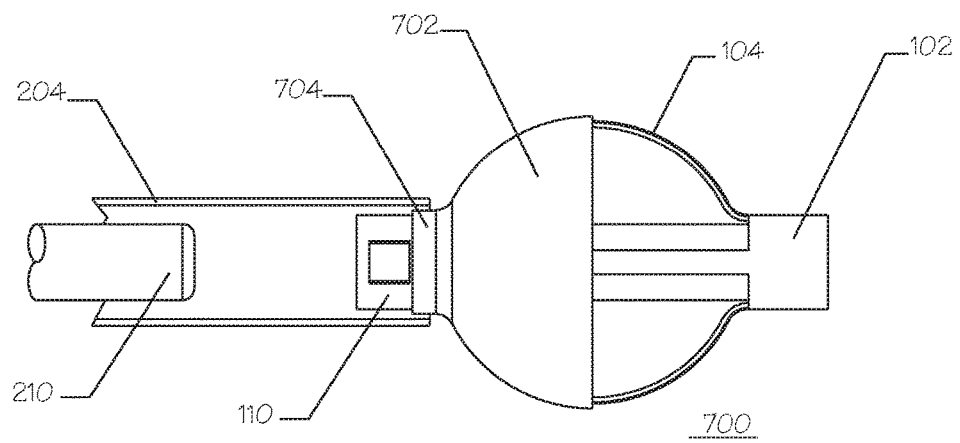
FIG. 13 illustrates a side view of an embolic implant comprising a plurality of radially expandable struts over which a membrane has been affixed.

FIG. 13 illustrates a side view of an implant 700 having been released from the delivery catheter tube 210 but still residing proximate the guide catheter tube 204, which is shown in cross-section. The implant 700 comprises the distal end 102, the plurality of struts 104, the proximal end 110, a covering 702, and a proximal covering bond 704. The covering 702 is affixed to the proximal end 110 by the bond 704. The covering 702 can be elastomeric and be resiliently biased against the struts 104 or it can be adhered thereto.

Figure 14:
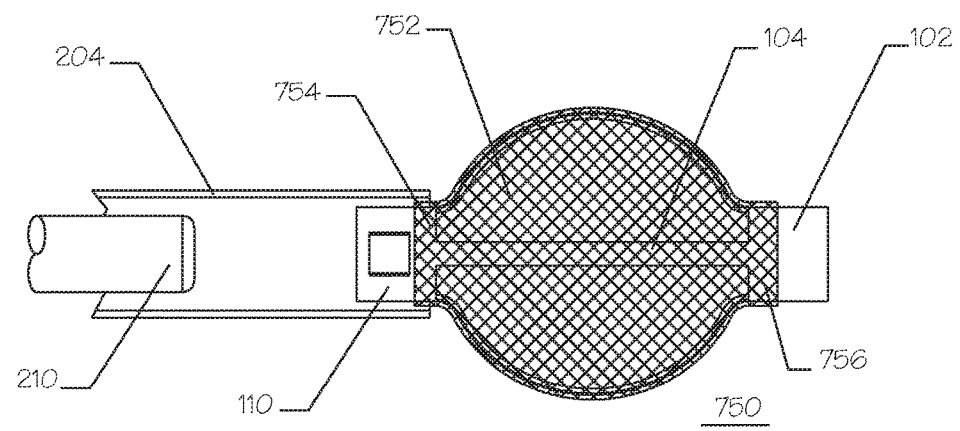
FIG. 14 illustrates a side view of an embolic implant comprising a porous mesh disposed over, and affixed to, the expandable struts.

FIG. 14 illustrates a side view of an implant 750 comprising the distal end 102, the plurality of struts 104, the proximal end 110, a covering 752, a proximal covering bond 754, and a distal covering bond 756. The implant 750 has been released from the delivery catheter 210 and its proximal end resides still partially within the distal end of the guide catheter tube 204. The proximal end 110, the struts 104, and the distal end 102 are similar to the implant 700 of FIG. 7A. The covering 752, as illustrated, comprises a mesh or fabric. The covering 752 can comprise structures such as, but not limited to, a weave, a braid, a knit, a membrane with macroscopic holes or pores, and the like. The covering 752 surrounds substantially all, or 100% of the surface of the implant 750. The proximal end 110 can project out from underneath the covering 752 to promote or facilitate engagement and fixation to the delivery catheter tube 210.

Figure 15:
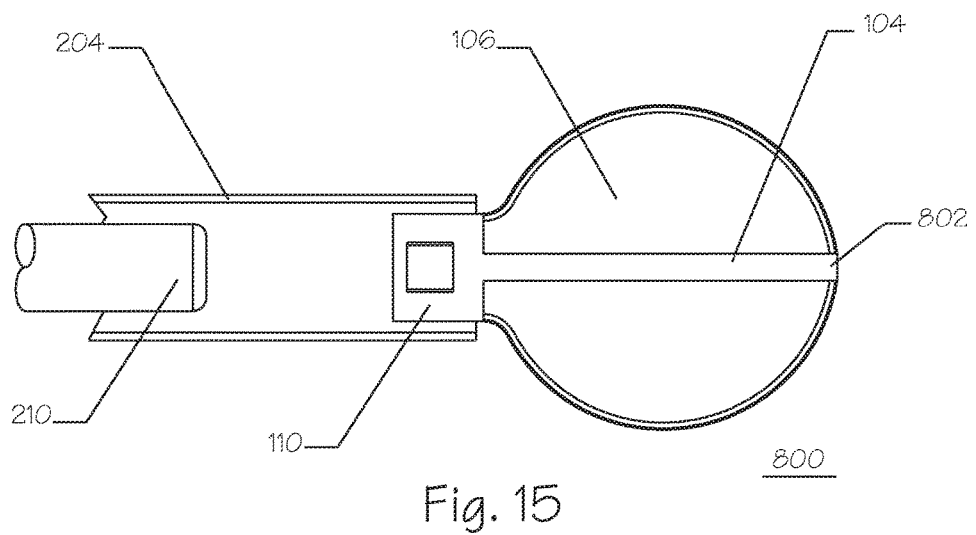
FIG. 15 illustrates a side view of an embolic implant comprising a plurality of struts affixed to a cylindrical proximal end and coming together at the distal end such that substantially nothing projects distally of the struts.

FIG. 15 illustrates a side view of an expanded embolic implant 800 having just been released from its delivery catheter 210 and still proximate the guide catheter tube 204, which is illustrated in cross-section. The implant 800 comprises a distal end 802, a plurality of struts 104, a proximal end 110, and a plurality of gaps 106. The struts 104 are integral to, or affixed to, the proximal end 110, which is configured as a short cylinder. The plurality of struts 104 are affixed to each other at the distal end 802. There is substantially no distal projection beyond where the struts 104 are affixed to each other. This implant design 800 is suitable for placement in an aneurysm within the cerebrovasculature. Berry aneurysms are configured such that the distal end 802 can be inserted into the aneurysm and the implant can be released from the delivery catheter at that point. The unitary structure of the struts 104 can also be comprised by the proximal end 110.

Figure 16:
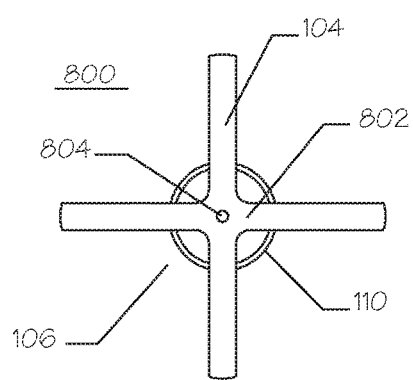
FIG. 16 illustrates an end view of the embolic implant of FIG. 8A showing how the struts come together at the distal end.

FIG. 16 illustrates a view of the implant 800 of FIG. 8A as seen looking toward the distal end 802. The implant 800 comprises the plurality of struts 104, the proximal end 110, the distal end 802, the plurality of gaps 106, and an indexing hole 804. The implant 800 is configured so as to be smooth and unsharp in the distal end 802 such that the distal end 802 can be inserted into a cerebrovascular aneurysm and deployed therein without causing trauma to the fragile tissues of the aneurysm. The indexing hole 804 can be engaged by a linkage or rod (not shown) disposed within the lumen of the delivery catheter, and configured for manipulation at the proximal end of the delivery catheter, to move the distal end of the implant 800 away from the proximal end 110, stretching the implant 800 longitudinally, and causing the struts 104 to collapse radially during placement. Removal of the linkage or rod can cause the struts 104 to assume their arcuate shape and expand. Referring to FIGS. 11 and 12, the linkage or rod can replace the guidewire 206 for the purposes of engaging and disengaging the releasable locking mechanism 202 from the latch feature 108 of the implant 800. The implant 800 can comprise between 2 and 20 struts 104 and can further comprise coverings 702 and 752 as illustrated in FIGS. 13 and 14. The implant 800 can be constructed from flat metal that is cut with the struts 104 formed into a star pattern, then bent around and affixed to the proximal end 110 by welding, fasteners, adhesives, or other fixation technique.

Figure 17:
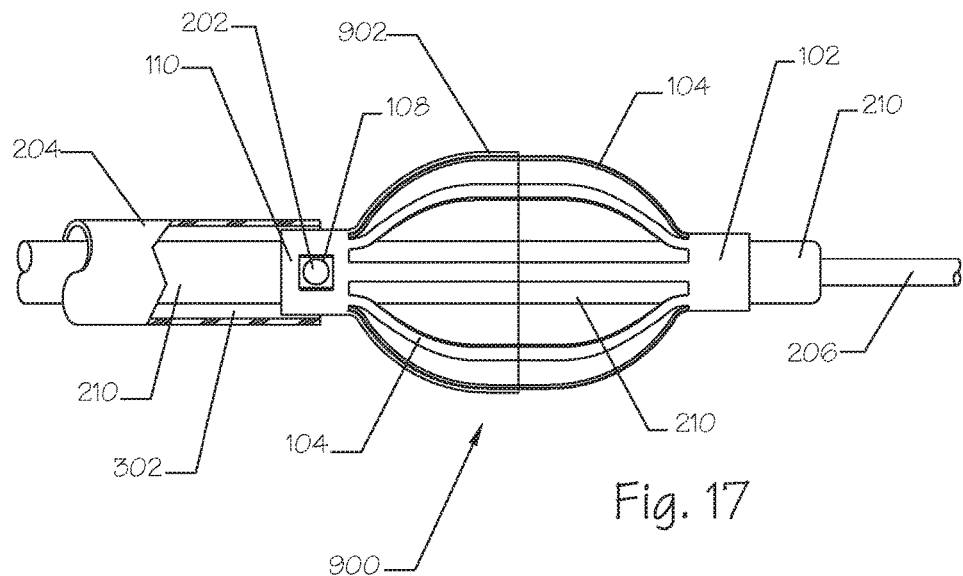
FIG. 17 illustrates a side view of an expanded embolic implant still connected to its delivery catheter, with its delivery sheath partially retracted and shown in cross-section, wherein the implant comprises a plurality of longitudinally disposed struts or bars connected together at the proximal and distal end and further including a thin, polymeric membrane surrounding the proximal portion of the implant.

FIG. 17 illustrates a side view of an expanded embolic implant 900 comprising a plurality of longitudinal struts 104, a proximal end 110, a distal end 102, a lock window 108 and a membrane covering 902. The implant 900 is releasably affixed to a delivery catheter 210 further comprising a releasable lock 202. The delivery catheter 210 is disposed over a guidewire 206 running through a delivery catheter 210 central lumen (not shown) while the delivery catheter 210 is inserted through a guide catheter or sheath 204 further comprising a guide catheter lumen 302. The delivery catheter 210 is routed through the open central lumen (not shown) of the proximal end 110 and the distal end 102 of the implant 902 to project distally of the distal end 102. The guidewire 206 projects out the distal end of the delivery catheter 210 and resides within a central lumen (not shown) comprised by the delivery catheter 210. The embolic implant 900 has been exposed outside the lumen 302 of the introducer sheath or guide catheter 204 and is unconstrained such that diametric expansion is possible. The longitudinal slats 104 are generally compressed prior to this expansion and aligned substantially axially or longitudinally with respect to the catheter 210. Once expanded, as illustrated, the ribs or slats 104 are biased to form arcuate shapes near the proximal end 110 and the distal end 102. The central region of the ribs or slats 104 remains generally straight and aligned longitudinally. The proximal region of the slats 104 is covered with a membrane 902. The membrane 902 can cover the distal end of the slats 104 and not the proximal end. The membrane 902 can cover both the proximal end and the distal end. The membrane 902 can cover the entire region of the implant 900 which is comprised by the slats 104. The membrane 902 can be fabricated from materials described within this document.

Figure 18:
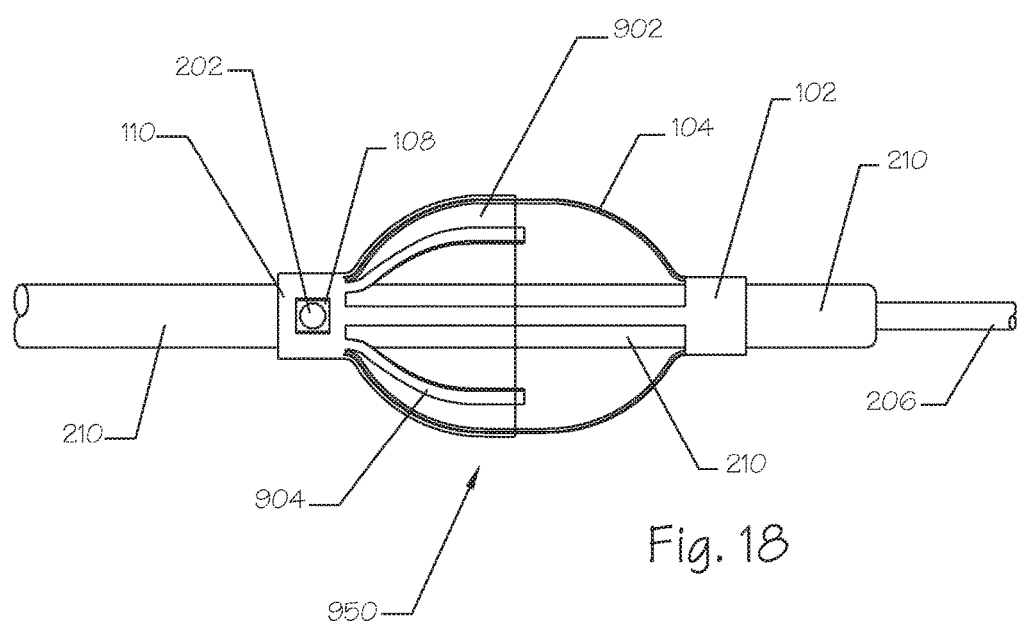
FIG. 18 illustrates a side view of an expanded embolic implant still connected to its delivery catheter but with the delivery sheath retracted out of the illustration, wherein the embolic implant comprises a plurality of longitudinally disposed struts interdigitated with a plurality of partial longitudinal struts and further partially covered with a membrane.

FIG. 18 illustrates a side view of a diametrically expanded embolic implant 950 still attached to its delivery catheter 210. The sheath 204 of FIG. 9A has been removed. The embolic implant 950 comprises the proximal end 110, the distal end 102, a locking window 108, a plurality of longitudinally projecting bars or struts 104, and a plurality of partial longitudinally projecting bars or struts 904 affixed only to the proximal end 110. The embolic implant 950 further comprises a membrane 902 covering the proximal portion of the embolic implant 950. The catheter 210 further comprises the releasable lock 202, a guidewire lumen (not shown), and a guidewire 206. The partial struts, ribs or slats 904 affixed to the proximal end 110 of the implant 950 project substantially to the center of the implant 950 but they can extend within any range from about 10% to 90% of the way to the distal end 102. The partial struts 904 can be affixed to the distal end 102 and be unconnected from the proximal end 110 with the same amount of projection in the opposite direction as described for partial struts 904 affixed to the proximal end 110. The implant 950 can comprise the membrane 902, optionally disposed over the proximal end and extending substantially the length of the partial struts 904. Full length struts 104 provide structural control over the overall diameter and length of the implant 950. The partial struts 904 can project substantially the same radial distance outward as the full length struts 104, or they can project further radially, or they can project less far, radially, than the full length struts 104. The full length struts 104 and the partial struts 904 can comprise the same materials, or they can comprise different materials or the same materials but with different properties.

Figure 19:
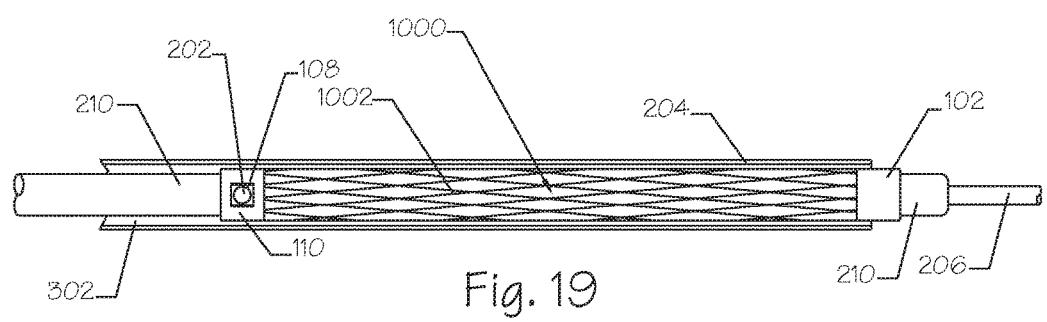
FIG. 19 illustrates a side view of a collapsed embolic implant attached to its delivery catheter and disposed within its delivery sheath, wherein the implant comprises a mesh.

FIG. 19 illustrates a side view of a radially collapsed embolic implant 1000. The implant 1000 comprises the proximal end 110, the distal end 102, the lock window 108, and the mesh 1002. The implant 1000 system also comprises the delivery catheter 210 further comprising the releasable lock 202, the guidewire lumen (not shown) and the guidewire 206. The implant 1000 system further comprises a delivery sheath or guide catheter 204, which is shown in cross-section. The mesh 1002 is constrained radially within the lumen 302 of the guide catheter or delivery introducer 204. The proximal end 110 of the implant 1000 remains affixed to the delivery catheter 210 by way of the lock 202 on the delivery catheter 210 being engaged into the locking feature 108, which is a rectangular opening in the proximal end 110. The guidewire 206 is illustrated as remaining in place, which is generally the case, and is used to assist guiding the delivery catheter 210 through the vasculature to the target treatment area.

Figure 20:
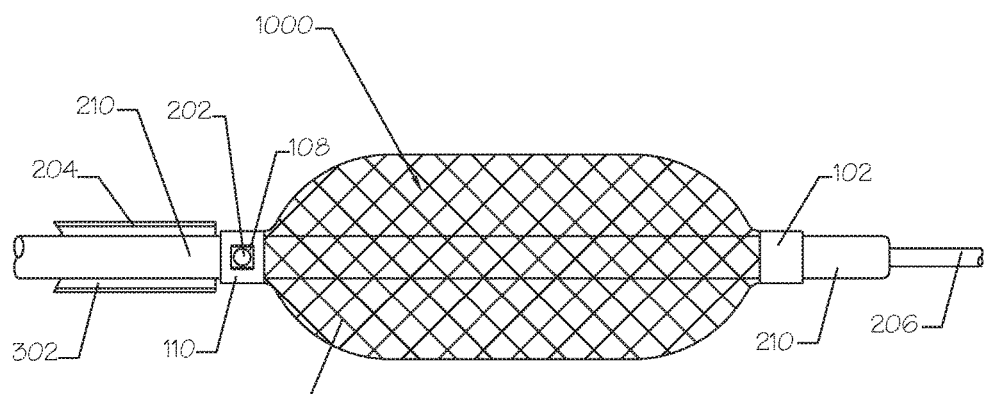
FIG. 20 illustrates a side view of the embolic implant of FIG. 19 wherein the sheath has been withdrawn to expose the implant allowing it to expand diametrically.

FIG. 20 illustrates a side view of the embolic implant 1000 from FIG. 19 following radial expansion. The embolic implant 1000 comprises the mesh 1002, the proximal end 110, the distal end 102, and the proximal lock window 108. The embolic implant 1000 system also comprises the sheath 204, the delivery catheter 210 further comprising the guidewire lumen (not shown), the releasable lock 202, and the guidewire 206. The mesh 1002 of the embolic implant 1000 has expanded to its full operational diameter. The mesh 1002 can comprise a self-expanding, spring biased material, it can comprise a malleable, balloon expandable material, a malleable material that is diametrically expanded by axial compression of the distal end 102 toward the proximal end 110, it can comprise shape memory materials that are activated at body temperature, shape memory materials that are activated by Ohmic heating to temperatures above body temperature, it can comprise materials that exist or transition into a superelastic or pseudoelastic state, or the like. The mesh 1002 can comprise wires of round, rectangular, oval, triangular, or other geometric cross-section. The expanded mesh 1002 can comprise an outer diameter of between about 1.1 and 10 times that of the collapsed implant 1000 of FIG. 10A. The sheath 204 is shown retracted to expose the proximal end 110. The delivery catheter 210 remains affixed to the implant 1000 by way of the releasable lock 202, which is affixed to the delivery catheter 210, being engaged into the locking feature 108 on the proximal end 110. The guidewire 206 remains in place within the lumen (not shown) of the delivery catheter 210.

Figure 21:
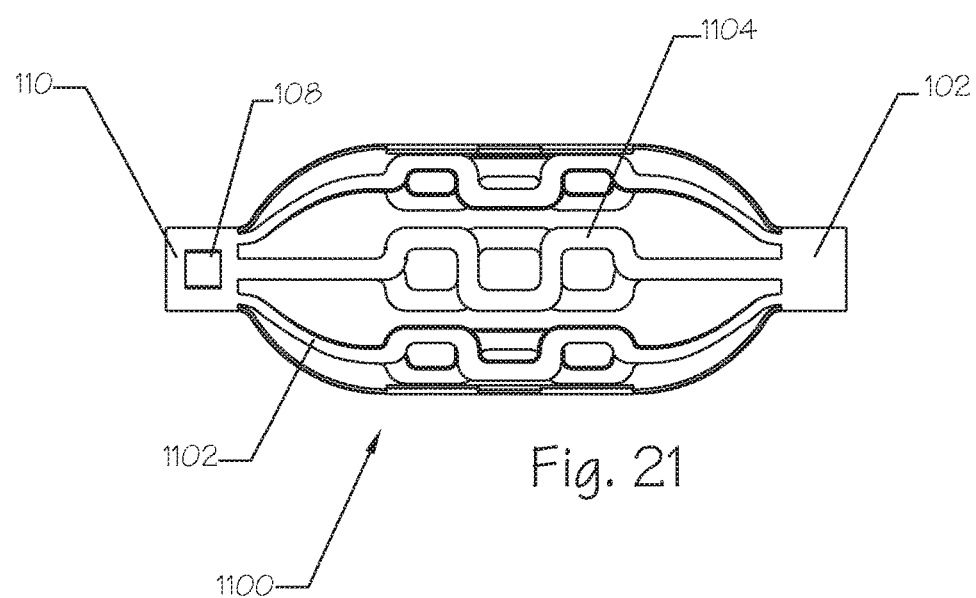
FIG. 21 illustrates a side view of an embolic implant totally separated from its delivery catheter and sheath wherein the embolic implant comprises a plurality of longitudinal struts further comprising a plurality of serpentine segments in the center region of the longitudinal struts.

FIG. 21 illustrates a side view of a diametrically expanded embolic implant 1100 alone without any of its associated delivery catheters or sheaths, which are the same as those described herein for other embodiments. The expanded embolic implant 1100 comprises the proximal end 110, the distal end 102, a plurality of longitudinally oriented bars or stays 1102, the locking feature 108, and a plurality of serpentine central regions on the longitudinal bars or stays 1102. The longitudinal struts 1102 are affixed or integral to the proximal end 110 and the distal end 102. The longitudinal struts 1102 are formed integrally with, or affixed to, the serpentine central strut area 1104. The serpentine central strut area 1104 can comprise a single undulation, or a plurality of undulations ranging from about 1 to about 20 undulations. In the illustrated embodiment, a total of 8 struts are present. The locking feature 108 can be integrally formed with the proximal end 110, the distal end 102, or both. The locking feature 108 can comprise structures other than a window in generally cylindrical thin walled structures such as is illustrated herein. Such other locking features 108 can comprise projections, wells, fasteners, bayonet mounts, friction interference, and the like.

Figure 22:
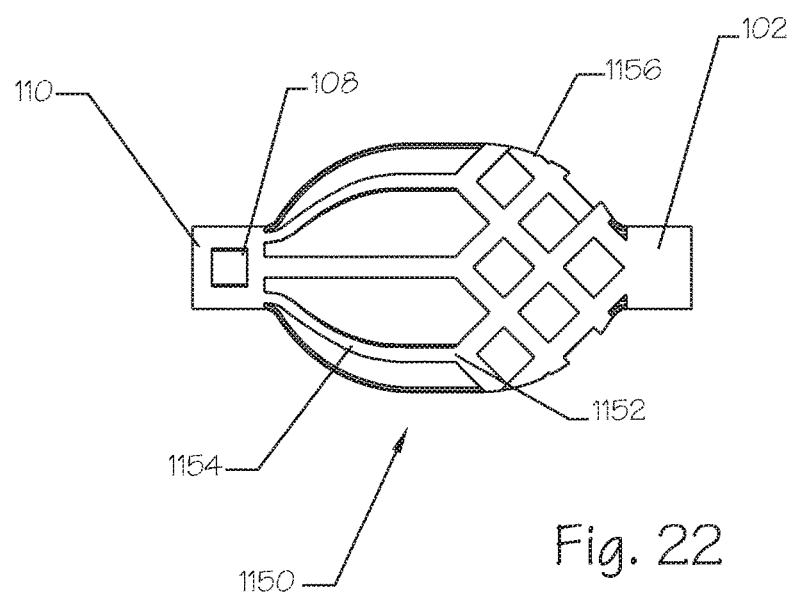
FIG. 22 illustrates a side view of an embolic implant totally separated from its delivery catheter and sheath, wherein the implant comprises a plurality of longitudinally disposed struts in its proximal central region and a mesh in its distal central region.

FIG. 22 illustrates a side view of a diametrically expanded embolic implant 1150. The embolic implant 1150 further comprises the proximal end 110, the distal end 102, the locking feature 108 a plurality of proximal longitudinally oriented struts or stays 1154, and a distal mesh 1156, and a connecting region 1152 between the struts 1154 and the mesh 1156 elements. The longitudinal struts 1154 are affixed, or integral to, the proximal end 110. The distal mesh 1156 is affixed, or integral to, the distal end 102. The longitudinal struts 1154 are affixed to the mesh 1156 at a plurality of connector points 1152 which can be welded, fastened, or formed integrally with the mesh 1156 and the struts 1154. The mesh 1152 is illustrated as occupying approximately ½ of the distance between the proximal end 110 and the distal end 102 but it could occupy anywhere between 10% and 90% of the distance. The mesh 1156 can be at the distal end, as illustrated, or it can be at the proximal end.

Figure 23:
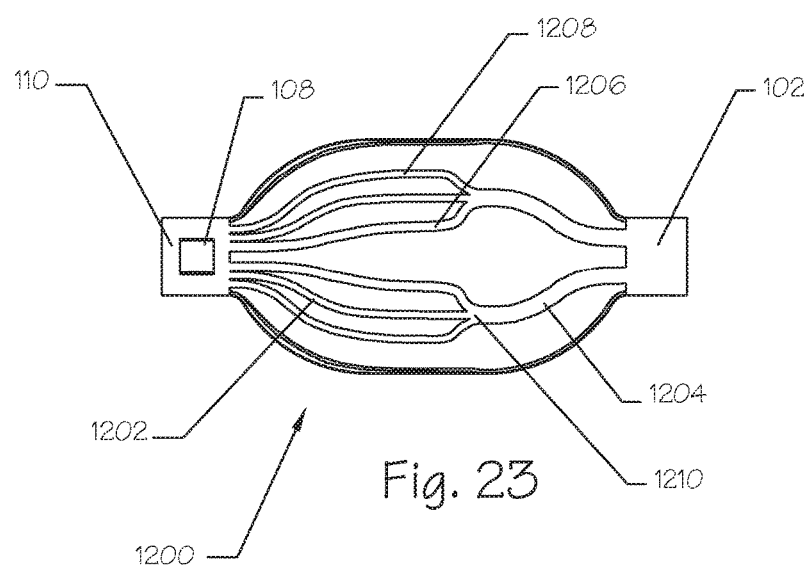
FIG. 23 illustrates a side view of an embolic implant comprising a plurality of longitudinal struts that each divide into three struts with the division point being in the central region of the implant.

FIG. 23 illustrates a side view of an expanded embolic implant 1200 comprising the proximal end 110 further comprising the locking feature 108, the distal end 102, a plurality of distal longitudinally projecting struts or bars 1204, a plurality of thinner, proximal longitudinally projecting struts or bars 1208, 1206, 1202 affixed to the proximal end and to a connector point 1210 at the proximal end of the distal struts 1204. The longitudinal struts in the distal end 1204 are larger than the struts 1202, 1206, and 1208 in the proximal end, but they can also be approximately the same cross-section or smaller in size. The larger distal struts 1204 are affixed, or integral to, the smaller proximal struts 1202, 1206, 1208 in the connection zone 1210. As illustrated there are three small proximal struts 1202, 1206, and 1208 for each larger distal strut 1204. The number of proximal struts can range from one to about 5 or more for each distal strut 1204. The orientation can also be reversed such that the smaller number of larger struts 1204 are affixed or integral to the proximal end with the smaller struts, of greater plurality, are affixed to the distal end.

Figure 24:
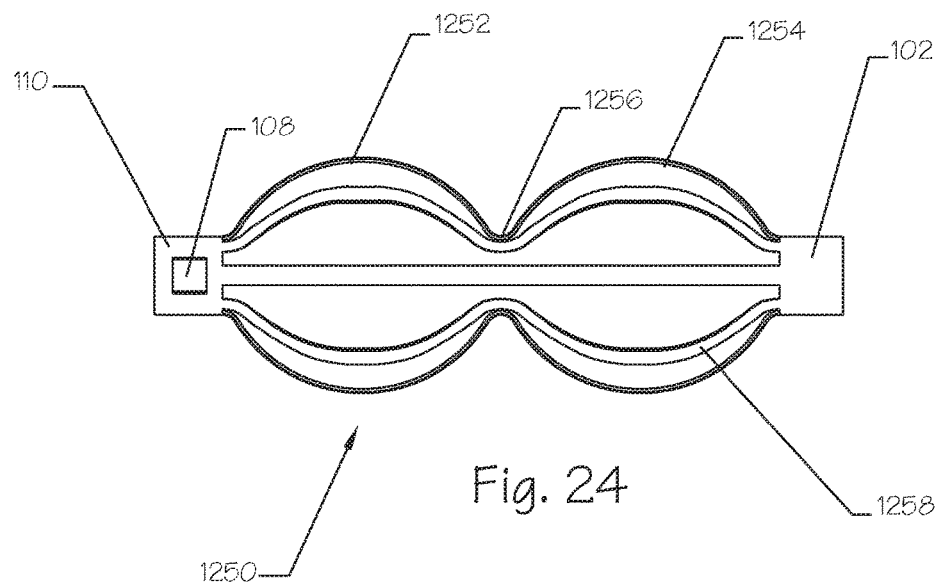
FIG. 24 illustrates a side view of an embolic implant comprising a plurality of longitudinal struts formed to generate two bulbs connected near the center of the implant in a smaller diameter region.

FIG. 24 illustrates a side view of a laterally expanded embolic implant 1250 comprising the proximal end 110 further comprising the locking feature 108, the distal end

102, a proximal lobe 1252 comprising a plurality of struts 1258, and a distal lobe 1254 comprising a plurality of longitudinally disposed struts 1258. The proximal lobe 1252 and the distal lobe 1254 are affixed to each other in the central connector region 1256. The longitudinal struts 1252 in the proximal region are affixed to, or integral with, the longitudinal struts in the distal region 1254. The proximal struts 1252 and the distal struts 1254 can be affixed or integral to each other at the connection zone 1256 or at any other convenient location. As illustrated the connection zone 1256 is configured to a smaller diameter than the maximum diameter of the proximal lobe 1252 or the distal lobe 1254. The maximum diameter of the proximal lobe 1252 can be greater than that of the distal lobe 1254, it can be smaller, or it can be approximately the same. The struts comprising the proximal lobe 1252 and the distal lobe 1254 can be the same struts. The struts comprising the proximal lobe 1252 and the distal lobe 1254 can be affixed to, or integral with, the proximal end 110 and the distal end 102, respectively. The distal end 102 can comprise a locking feature 108 similar to that of the proximal end 110.

Figure 25:
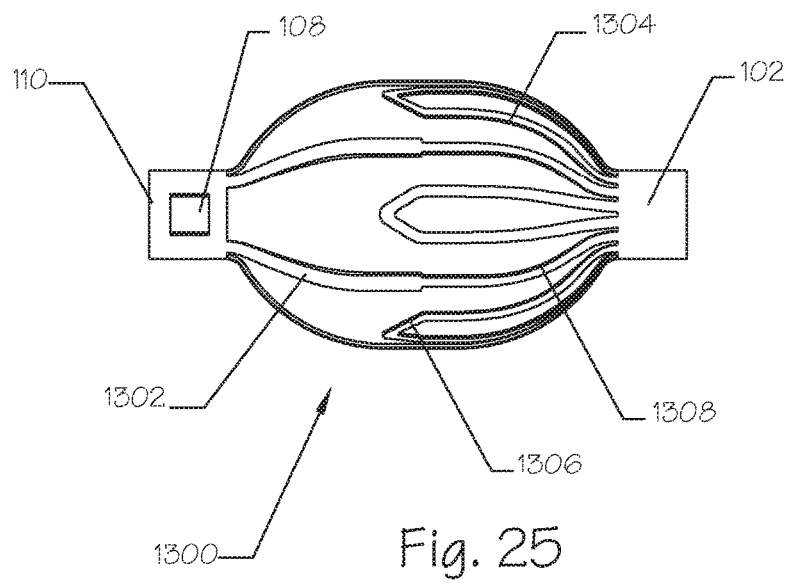
FIG. 25 illustrates a side view of an embolic implant comprising a plurality of longitudinal struts interdigitated with flower petal structures formed in outline by bent struts affixed to the distal end of the implant.

FIG. 25 illustrates a side view of an expanded embolic implant 1300 comprising the proximal end 110 further comprising the locking feature 108, the distal end 102, a plurality of proximal longitudinally projecting struts or bars 1302 which transition in the central zone to a plurality of complimentary thinner bars or struts 1308 in the distal region. Interdigitated between the distal longitudinal struts 1308 are a plurality of thin bars 1304 shaped as leaves or flower petals in a closed loop The tips 1306 of the flower petals 1304 are configured in a triangular shape and are bent slightly, radially outward. The longitudinal struts 1302 are larger in lateral dimension toward the proximal end 110 and smaller in lateral dimension toward the distal end 102. Smaller struts 1304, affixed or integral to the distal end 102 are formed into a loop or flower petal shape and project axially only partially toward the proximal end 110. The smaller struts 1304 are formed with a triangular end configuration which is bent slightly outward to enhance the ability of the implant 1300 to engage with a vessel wall, wall thrombus, atheroma, or the like. The triangular tip can follow the approximate shape of the implant 1300 or it can be bent outward or inward. The entire flower petal loop 1304 can also be configured to have an outward, or inward, projection beyond the general envelope of the implant 1300 to assist with stability in the target implant site. The flower petal loops 1304 and the distal longitudinal struts 1308 can have a smaller cross-section than that of the proximal longitudinal struts 1302 and similar to that of the distal longitudinal struts 1308. The flower petal loops 1304 can have similar or larger cross-sections than the proximal longitudinal struts 1302. The flower petal loops 1304 can be affixed to the proximal end 110 rather than the distal end 102.

Figure 26:
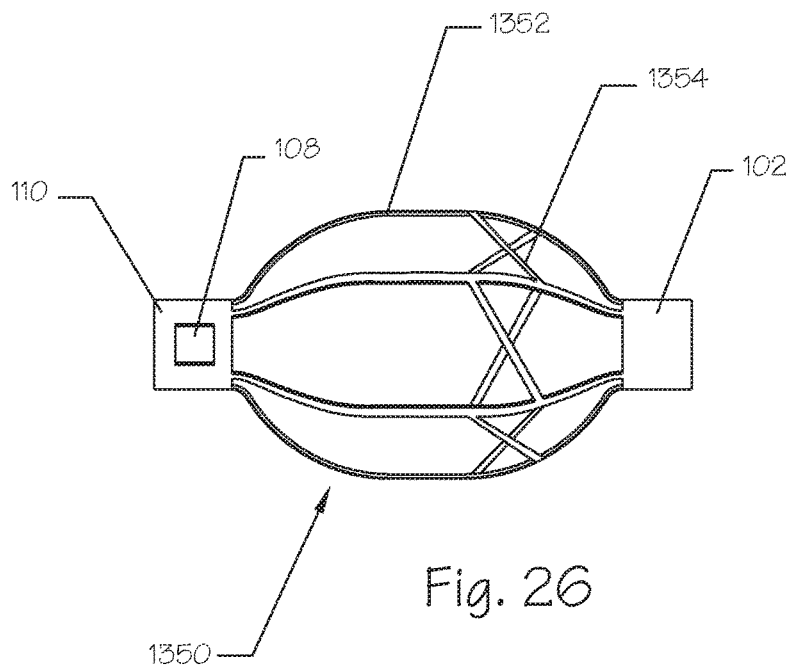
FIG. 26 illustrates a side view of an embolic implant comprising a plurality of longitudinal struts interconnected in the central region by laterally disposed bars.

FIG. 26 illustrates a side view of an expanded embolic implant 1350 comprising the proximal end 108 further comprising a locking feature 108, the distal end 102, a plurality of longitudinally oriented struts 1352, and a plurality of laterally projecting struts 1354. The axially oriented struts 1352 can be affixed at their proximal end to the proximal end 110 or they can be formed integrally thereto. At their distal end, the axially oriented struts 1352 can be affixed or integral to the distal end 102. The lateral struts 1354 can be integral to the axial struts 1352 or they can be affixed thereto using fasteners, welds, adhesive bonding, or the like. The lateral struts 1354 can have the same mechanical properties as the longitudinal struts 1352, e.g. shape memory, malleable, spring, or the like. The lateral struts 1354 can have different mechanical properties from those of the longitudinal struts 1352. The lateral struts can be straight, as shown, or they can have curvature or bends to accommodate compression of the space between the lateral struts 1352 when the implant 1350 is collapsed or compressed to its radially small diameter.

The longitudinal struts can comprise superelastic nitinol, while the lateral struts 1354 can comprise shape memory nitinol that retains martensitic properties when in the packaged state but which transition to superelastic properties at temperatures higher than room temperature. Typical temperatures that could generate phase transition from Martensite to Austenite would include those above room temperatures of about 22° C. to 25° C. to about body temperature of about 37° C. or somewhere therebetween. The illustration of FIG. 13B shows the implant 1350 with its lateral struts 1352 straightened but said struts 1352 would possess a serpentine, curved, or bent shape with the implant 1350 in its diametrically collapsed configuration such as prior to, and during introduction into the patient. The lateral struts 1354 can be near the proximal end, the distal end (as illustrated), toward, the center, or a plurality of lateral struts 1354 can connect the longitudinal struts 1352 in more than one place.

Figure 27:
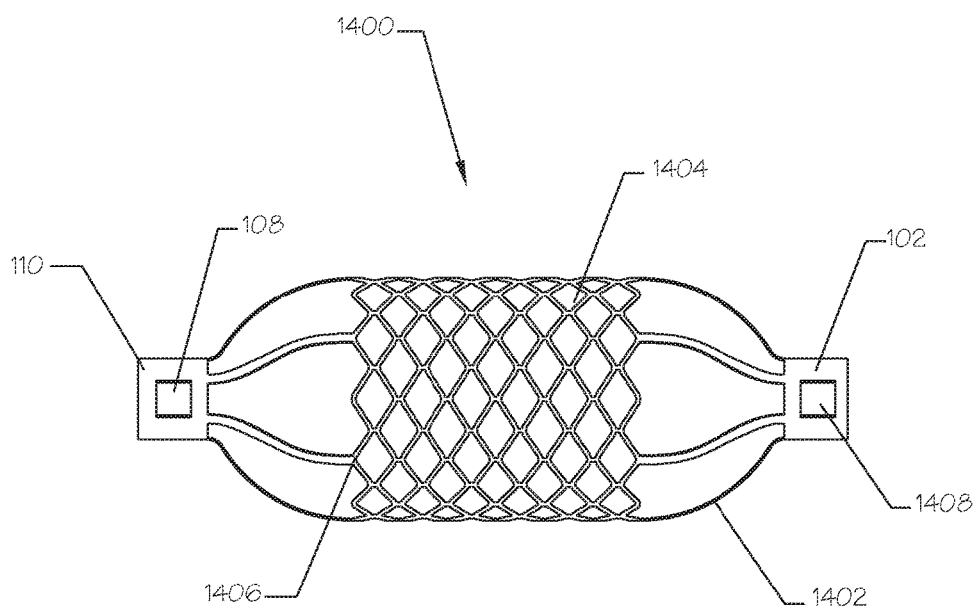
FIG. 27 illustrates a side view of an embolic implant comprising a plurality of longitudinal struts connecting a central mesh structure to the proximal and distal ends of the implant.

FIG. 27 illustrates a side view of an expanded embolic implant 1400 comprising the proximal end 108 further comprising a locking feature 108, the distal end 102 further comprising a distal locking feature 1408, a plurality of longitudinally oriented struts 1402 at the proximal end distal ends of the implant 1400, a central mesh 1404, and a plurality of connector regions 1406 wherein the central mesh 1404 is affixed to the ends of the struts 1402. The longitudinal struts 1402 are affixed to the proximal end 110 while the longitudinal struts 1402 at the distal end are affixed to the distal end 102. The proximal locking feature 108 is affixed to, or integral with the proximal end 110 while the distal locking feature 1408 is affixed to, or integral with the distal end 102. Both the proximal end 110 and the distal end 102 are hollow, axially elongate structures comprising a central lumen (not shown). The proximal locking feature 108, the distal locking feature 1408, or both, can comprise a fenestration in the proximal end 110 and the distal end 102, respectively. The fenestration can be rectangular (as shown) but it can also be round, oval, triangular, or any other geometric shape suitable for interconnection with a lock on a delivery catheter. The locking features 108 and 1408 can further comprise projections, bumps, threaded regions, quick releases, bayonet mounts, fasteners, or the like.

Figure 28:
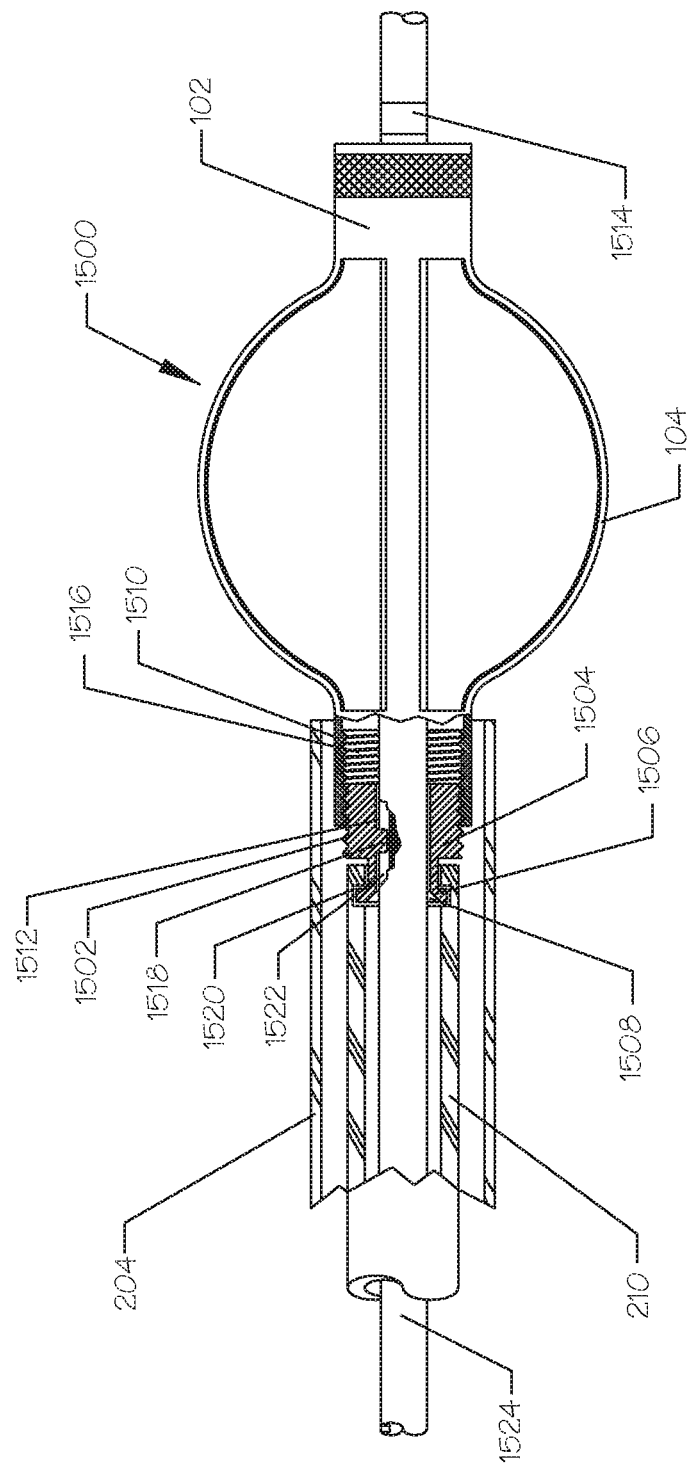
FIG. 28 illustrates a side, partial breakaway, view of an embolic implant coupled to a delivery catheter by means of a threaded, releasable linkage.

FIG. 28 illustrates a side cross-section and partial breakaway view of the embolic implant 1500 affixed to the distal end of the catheter tube 204. The embolic implant 1500 comprises the distal end 102 and the proximal end 1510 further comprising the internal threads 1516. The distal end of the catheter tube 204 further comprises a rotating coupler 1504, further comprising guidewire engaging projection 1518, a bearing flange 1506, a set of external threads 1502, an internal lumen 1512, and a tapered inlet 1508. The embolic implant 1500 system further comprises the delivery sheath, introduction sheath, or guide catheter 204, and a deployment guidewire 1524 further comprising a longitudinal groove 1522 and an optional guidewire radiopaque marker 1514. The catheter tube 204 further comprises a rotational bearing groove 1520. The implant 1500 comprises a plurality of longitudinally oriented slats, bars, runners, or the like 104. The rotating coupler 1504 is affixed, or integral to, the bearing flange, the external threads 1526, and the guidewire engaging projection 1518. The external threads 1502 of the rotating coupler 1504 engage with complementary internal threads 1516 on the implant 1500. Rotation of the rotating coupler 1504 relative to the implant 1500 causes increased longitudinal engagement or decreased longitudinal engagement, depending on the direction of the rotation.

In another embodiment, instead of threads, the rotating coupler 1504 can comprise a prong or projection (not shown) that engages with a circumferential slot (not shown) on the proximal end 1510 of the implant 1500. The prong or projection (not shown) can be comprised by the implant 1500 while the bayonet groove can be comprised by the distal end of the catheter shaft 204 or the rotating coupler 1504. The rotational coupling system can be comprised by the distal end 102 of the implant 1500 instead of the proximal end 1510.

A mechanism is provided to prevent rotation of the implant 1500 while the rotating coupler 1504 is being twisted. The rotation prevention mechanism can comprise structures and means including, but not limited to, a friction fit between the implant 1500 and the guide catheter 204, a separate stabilization linkage, operable from the proximal end, that engages with a hole, groove, or receptacle and locks the implant 1500 to prevent rotation about its longitudinal axis, and the like. The implant 1500 can further comprise a projection (not shown) that engages a longitudinal slot (not shown) in the distal end of the guide catheter 204 tubing. The projection is capable of axial slidable movement within the slot but is constrained against rotational motion by interference with the walls of the slot. The guide catheter 204 can comprise the projection while the implant 1500 can comprise the slot. The guide catheter 204 can comprise internal runners that project inwardly and engage with the spaces between the longitudinal slats 104 of the unexpanded implant 1500. The implant 1500 can be pushed out of the guide catheter tube 204 by axial or longitudinal distal movement of the catheter tubing 210 relative to the guide catheter tube 204.

Figure 29:
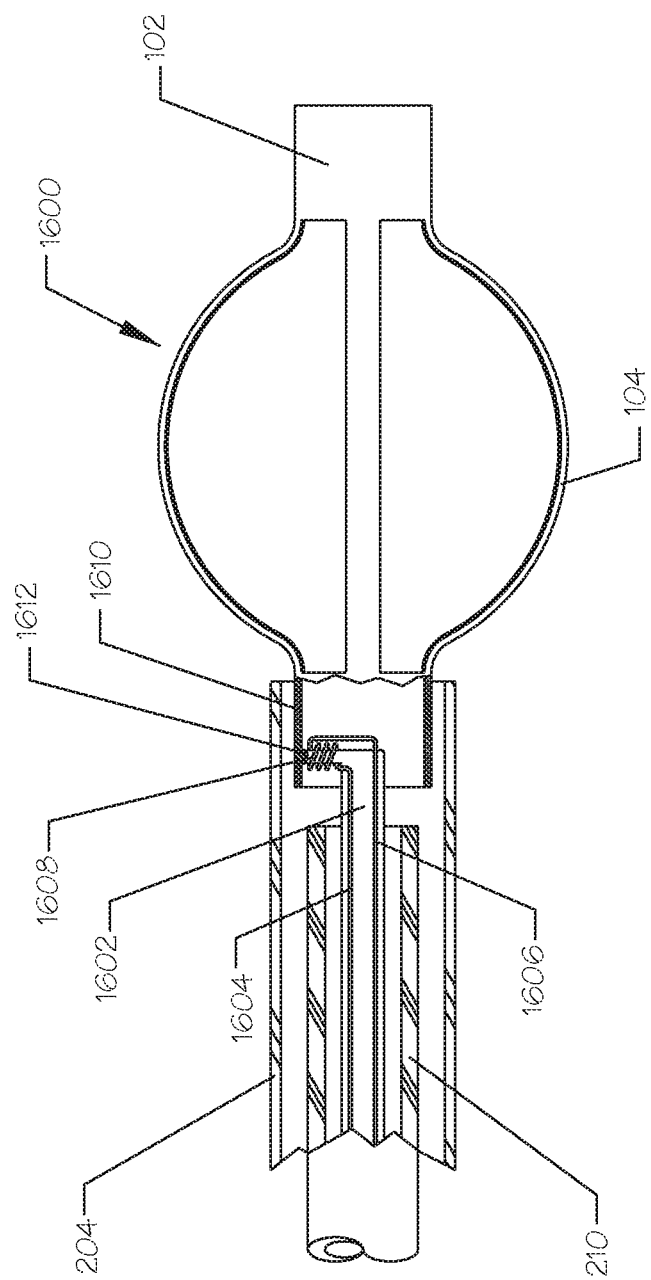
FIG. 29 illustrates a side, partial breakaway, view of an embolic implant coupled to a delivery catheter by means of a meltable linkage.

FIG. 29 illustrates a side, partial breakaway, view of an embolic implant 1600 comprising a plurality of axially oriented struts 104 affixed to the distal end 102 and to the proximal end 1610. The embolic implant 1600 further comprises the delivery catheter tube 210, the guide catheter 204, a pusher 1602 further comprising a first electrical lead 1604, a second electrical lead 1606, a resistive heating coil 1608, and a fusible link 1612. The fusible link 1612 is affixed, or integral to, the distal end of the pusher 1602. The fusible link 1612 can comprise a low temperature meltable metal such as solder, or a polymer material such as polypropylene, polyethylene, polyester, or the like. The fusible link 1612, as illustrated, is affixed to the implant 1600 in the region of the proximal end 1610 but it can also be affixed to the implant 1600 at the distal end 102. The resistive heating element 1608 can comprise materials such as tungsten, nickel chromium wire, or the like. The resistive heating element 1608 can be wrapped around the fusible link 1612 in the form of a coil, as illustrated, or it can be oriented longitudinally or in any other configuration in sufficiently close proximity as to transfer enough heat to melt the fusible link 1612. It is generally beneficial to shield the body from the heat of the resistive heating element 1608 and that is accomplished by insulation provided or comprised by the guide catheter tube 204 and the implant proximal end 1610. The pusher 1602 can be used to physically push the implant 1600 away from the guide catheter 204 to ensure complete deployment and release. The system can further comprise a guidewire 206 of FIG. 4, for example, if desired.

A hydraulically detachable linkage can comprise a fluid channel running from the proximal end of the delivery catheter to the distal end. The fluid channel can be operably connected to a piston, bladder, expandable member, or other structure that can force a releasably coupled implant from the distal end of the delivery catheter to cause release of the implant. The fluid channel is preferably pressurized with a liquid such as saline, radiopaque contrast media, or the like. Pressures of above 1,000 PSI can be generated using a small syringe and hand pressure applied by the operator to a pressurization port at the proximal end of the delivery catheter that is operably connected to the fluid channel. Pressures nearing 1,000 PSI or higher can force an implant, friction coupled to the distal end of the delivery catheter to become disconnected, detached, or otherwise released. The fluid pressure can be delivered into a space just proximal to the implant such that pressurization of the space forces the implant to move distally and disconnect from the delivery catheter. The space is operably connected to the fluid channel.

Figure 30:
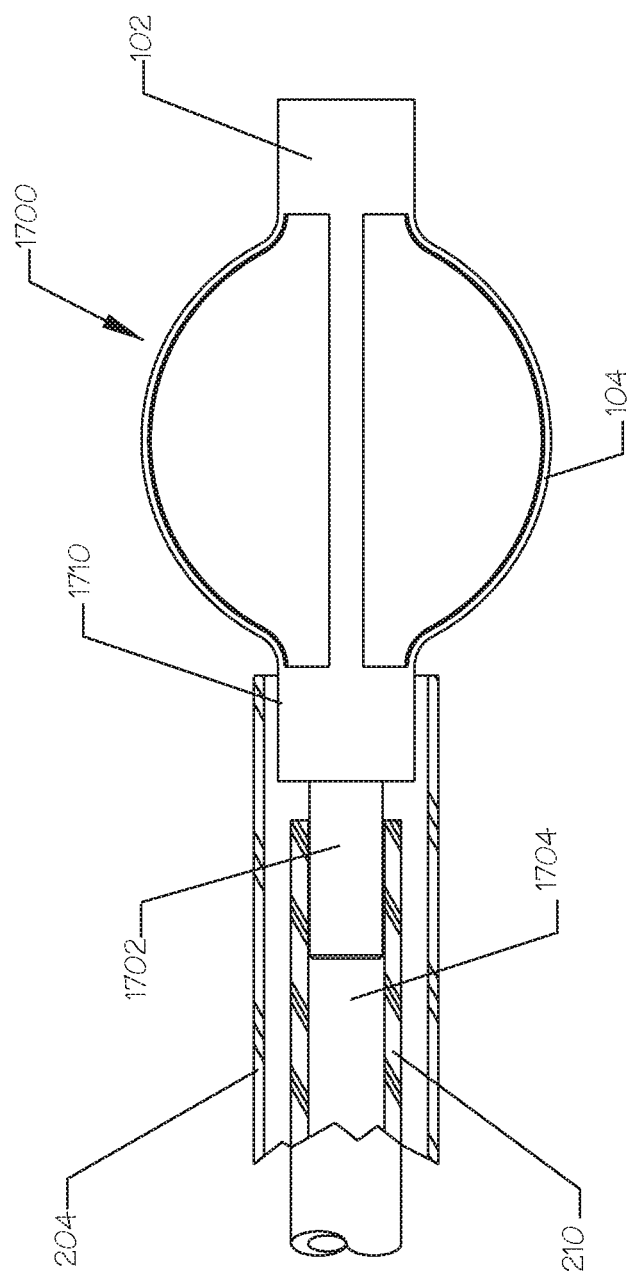
FIG. 30 illustrates a side, partial breakaway, view of an embolic implant coupled to a delivery catheter by means of a pressurized release system.

FIG. 30 illustrates a side view, in partial breakaway, of an embolic implant 1700 comprising a distal end 102, a proximal end 1710, and a piston 1702. The system further comprises the guide catheter 204, and the delivery catheter sheath 210 further comprising the pressurization lumen 1704. The implant 1700 has expanded to its full expanded operational diameter and the piston 1702 has just begun moving distally to separate the implant 1700 from the catheter 210. The piston 1702 is affixed to the proximal end 1710. The piston 1702 projects axially into the pressurization lumen 1704 and is slidably constrained to move only longitudinally therein. The piston 1702 is fluidically sealed to the walls of the catheter 210 such that pressure generated within the lumen 1704 does not leak out around the piston 1702. Fluid suitable for pressurization of the lumen 1704 can comprise materials such as, but not limited to, water, radiopaque contrast media, ethanol, and the like. The fluid is preferably an incompressible fluid so as not to cause pressure storage within the fluid, the release of which could be damaging to the instrumentation or the patient. Pressures suitable for pressurization of the lumen 1704 can range from about 10 PSI to about 3,000 PSI, all of which can be generated with a hand-held syringe. The higher pressures are often necessary to overcome the pressure losses within the small diameter lumen 1704, which can range from about 0.005 inches to about 0.050 inches but generally ranges from about 0.010 to about 0.030 inches in diameter. The length of the catheter tubing 210 is generally very long and can range from about 45 cm to about 250 cm with a preferred length of about 80 cm to about 150 cm for cerebrovascular access procedures.

The piston can comprise a bellows structure (not shown) that ensures that fluid pressure loss will not occur when the pressurization lumen 1704 is pressurized with fluid. The piston 1702 can further comprise piston rings or seals (not shown) to further inhibit pressure loss while the piston is being ejected or expelled from the distal end of the catheter tube 210. The piston can drive a latch, catch, releasable lock, or other structure that grasps a portion of the implant 1700. By driving the latch, the piston can unlock or unlatch the delivery catheter tube 210 from the proximal end 1710 of the implant 1700. The implant 1700 can further be driven off or separated from the delivery catheter tube 210 by distal relative movement of the guide catheter 204 or a separate pusher.

By similar means as that of the hydraulically detachable linkage, a vacuum linkage can be used to pull a vacuum at the distal end of the delivery catheter causing reduction in size or decreased projection of a coupling mechanism configured to releasably hold the implant secured to the delivery catheter.

Figure 31:
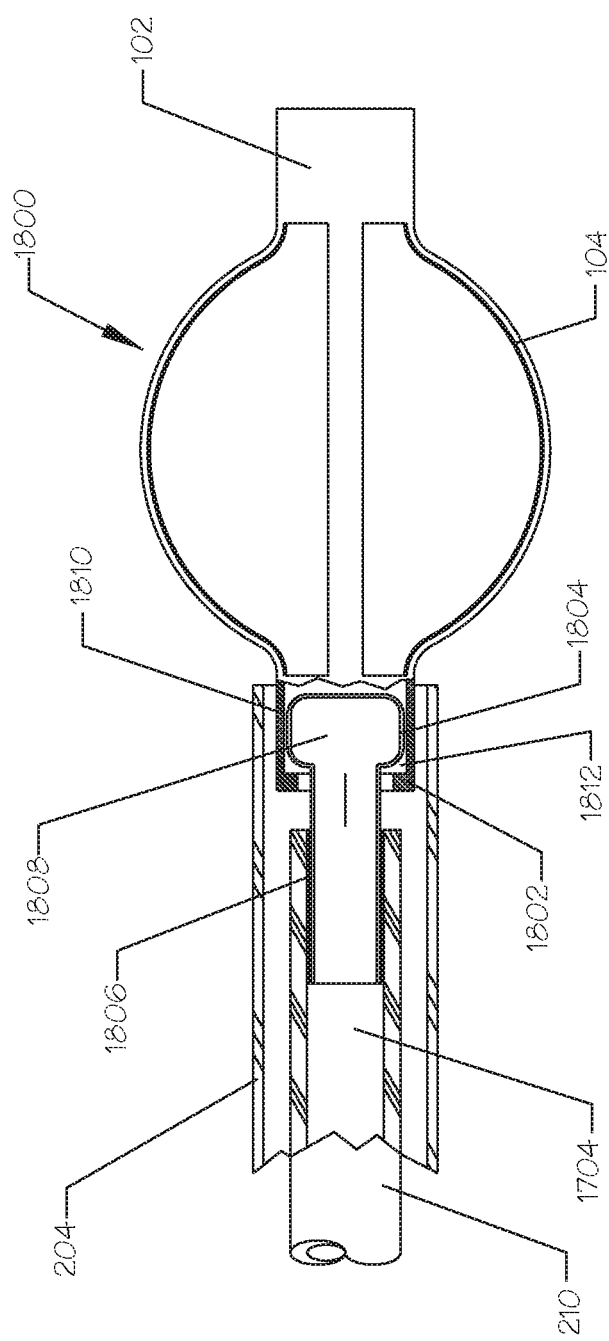
FIG. 31 illustrates a side, partial breakaway, view of an embolic implant coupled to a delivery catheter by means of an expandable coupler that can be decoupled by application of a vacuum within the coupler to shrink its diameter.

FIG. 31 illustrates a side view, in partial breakaway, of an implant 1800 comprising a distal end 102, a plurality of struts 104, and a proximal end 1810, further comprising an orifice 1802 and an inner lumen 1812. The system further comprises the delivery catheter 210 further comprising the pressure lumen 1704, the guide catheter 204, a bladder 1804 further comprising a bladder internal volume 1808, and a bladder bond 1806. The bladder 1804 is affixed to the distal end of the delivery catheter 210 by the bladder bond 1806. The bladder lumen 1808 is operably connected to the pressurization lumen 1704 and is otherwise fluidically sealed. The bladder 1804 can be constructed in its small profile and then be inflated to a diameter larger than that of the orifice 1802 or it can be constructed to be expanded to a diameter larger than that of the orifice 1802 in its unstressed state. Application of a vacuum or withdrawal of fluid from the bladder lumen 1808 by way of the pressurization lumen 1704 can reduce the lateral or diametric extent of the bladder 1804 to a size smaller than that of the orifice 1802 such that the implant 1800 is decoupled from the delivery catheter tubing 210. Further separation and deployment can be generated by distal movement of the guide catheter 204 relative to the delivery catheter tube 210.

Withdrawal of a vacuum, or removal of liquid or fluid, in the system described in FIG. 17 can pull the plug 1702 off the implant 1700, thus releasing and deploying the implant 1700. The plug 1702 can be friction fit or weakly snapped into a detent in the implant 1700 thus allowing for removability of the plug 1702, under vacuum applied to the pressurization lumen 1704.

A mechanical pusher can be activated at the proximal end of the delivery catheter to move axially and force a releasably coupled implant from the distal end of the delivery catheter. The mechanical pusher is generally disposed within a lumen of the delivery catheter to be radially constrained but longitudinally movable within the lumen. The mechanical pusher can be directly pushed or moved axially by way of mechanical advantage such as a lever or trigger mechanism. The mechanical pusher can also be rotated to generate a jack-screw effect thus generating linear motion at the distal end of the delivery catheter and forcing the implant to release or decouple.

Coupling of the implant at the distal end of the catheter can comprise a simple friction fit with the implant comprising an outer sleeve that tightly fits over a stub of the delivery catheter. The catheter stub projects into the sleeve of the implant, for example and is held there by a press-fit, binding fit, detents and projections, or the like.

FIG. 32 illustrates a side, partial breakaway, view of an implant 1900 that is releasably affixed to its delivery catheter tubing 210 by a pusher 1902. The implant 1900 comprises the distal end 102, a plurality of runners 104, a proximal end 1910 further comprising a bumper 1906 and engagement detents 1904. The system further comprises the delivery catheter tube 210 further comprising one or more projections 1912, one or more spring elements 1914, and the guide catheter tube 204. The proximal end 1910 is a substantially hollow, axially elongate structure affixed to the proximal end of the runners 104. Affixed to the interior of the proximal end 1910 is a bumper or region of reduced central opening 1906. Affixed to the distal end of the delivery catheter tube 210 are the one or more engagement prongs 1912 biased outward by one or more optional springs 1914. The engagement prongs 1912 are configured to engage with depressions or detents 1904 on the inside of the implant proximal end 1910. The engagement prongs 1910 cause a defeatable engagement that can be overcome by axial force applied by distal movement of the pusher 1902 against the bumper 1906. The springs 1914 are optional and the same functionality can be obtained from resiliency in the delivery catheter tube 210 or in the structure of the engagement prongs 1912. The detents 1904 on the inside of the proximal end 1910 can also be configured as holes or openings in the proximal end 1910 or as serrated or circumferentially grooved surfaces to grip the prongs 1912.

The implants can be affixed to the delivery catheter by magnetic means that can activated and deactivated by use of electromagnets powered from the proximal end of the delivery catheter 200 using electrical contacts such as those illustrated in FIG. 16.

The implant 100, when intended for cerebrovascular embolization, can have a diameter or lateral, unexpanded dimension of less than 0.021" (0.5334 mm). The implant 100 can have a length of about 0.2 to 0.3 inches in its unexpanded state. The wall thickness of the implant can range from about 0.001 to 0.005 inches. For neuro-interventional procedures in the cerebrovasculature, the expanded diameter of the implant 100 should range from about 2 mm to about 6 mm with a preferred range of about 3 mm to about 5 mm.

The implant 100 can further comprise coatings to enhance thrombogenicity or space-filling characteristics. Such coatings can comprise hydrophilic hydrogel or expandable foam which is applied to the implant 100 prior to use, and be allowed or caused to dry. Upon exposure to blood or other liquid, the hydrogel or foam absorbs water and swells in volume. Such volume swelling can increase the hydrogel or foam layer thickness up to ten times, or more. The hydrophilic hydrogel can comprise fibrin glue, prothrombin, or other blood clotting substance, or the blood clotting chemical, substance, or material can be applied to the implant 100 without the hydrogel.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:
1. An embolic implant comprising:
   a wire frame structure comprising:
      a pair of opposing zigzag segments including a plurality of V-shaped elements defining an open end, the V-shaped elements joined at the open end of the V-shaped elements via struts to form a central portion of the wire frame structure, the V-shaped elements defining proximal or distal vertices pointing proximally or distally away from a longitudinal center of the wire frame structure;
      a first plurality of longitudinally oriented struts extending from the proximally pointing vertices of the V-shaped elements, the first plurality of longitudinally oriented struts being joined together near a radial center of the wire frame structure at a proximal end of the wire frame structure; and a second plurality of longitudinally oriented struts extending from the distally pointing vertices of the V-shaped elements, the second plurality of longitudinally oriented struts being joined together near the radial center of the wire frame structure at a distal end of the embolic implant; and a blood impermeable membrane covering at least a part of the wire frame structure extending from the proximal end of the wire frame structure to at least distal to the longitudinal center of the wire frame structure.

2. The system of claim 1, wherein the struts joining the V-shaped elements are longitudinally displaced from each other.

3. The system of claim 1, wherein the proximal vertices of the V-shaped elements are not circumferentially aligned.

4. The system of claim 1, further comprising:
a first ring joining the first plurality of the longitudinally oriented struts together at the proximal end of the wire frame structure; and
a second ring joining the second plurality of the longitudinally oriented struts together at the distal end of the wire frame structure.

5. The system of claim 4, wherein at least one of the first ring or the second ring comprises a radiopaque material.

6. The system of claim 1, the blood impermeable membrane partially covering the wire frame structure, and the membrane comprising a proximal facing surface and a circumferential facing surface, wherein at least the proximal facing surface is blood impermeable.

7. The system of claim 6, wherein the proximal facing surface and the circumferential facing surface are blood impermeable.

8. The system of claim 6, wherein the blood impermeable membrane is perforated with weep holes.

9. The system of claim 6, wherein the blood impermeable membrane comprises expanded polytetrafluoroethylene (ePTFE) impregnated with an adhesive, the membrane being glued to the wire frame structure.

10. The system of claim 6, wherein the blood impermeable membrane comprises two layers of expanded polytetrafluoroethylene (ePTFE) impregnated with an adhesive, the membrane being glued to the wire frame structure.

11. The system of claim 1, wherein the wire frame structure is at least partially formed from a pseudoelastic metal alloy.

12. The system of claim 1, wherein the wire frame structure is configured to expand from a compacted configuration to a fully expanded configuration, wherein when the wire frame structure is in the fully expanded configuration, the wire frame structure has a maximum diameter of about 5 millimeters, and when the wire frame structure is in the compacted configuration, the wire frame structure has a maximum diameter of less than about 0.6 mm.

13. The system of claim 1, further comprising a delivery member, wherein the wire frame structure is releasably attached to the delivery member.

14. The system of claim 13, further comprising a detachment joint releasably joining a proximal end of the wire frame structure to the delivery member.

15. The system of claim 14, wherein the detachment joint is an electrolytic detachment joint.

16. A method for occluding an artery, the method comprising:
advancing a delivery catheter through vasculature of a patient, wherein the delivery catheter houses an embolic implant within a distal tip of the delivery catheter, the embolic implant comprising:
a self-expanding wire frame structure comprising:
a pair of opposing zigzag segments including a plurality of V-shaped elements defining an open end, the V-shaped elements joined at the open end of the V-shaped elements via struts to form a central portion of the wire frame structure, the V-shaped elements defining proximal or distal vertices pointing proximally or distally away from a longitudinal center of the wire frame structure;
a first plurality of longitudinally oriented struts extending from the proximally pointing vertices of the V-shaped elements, the longitudinally oriented struts being joined together near a radial center of the wire frame structure at a proximal end of the embolic implant; and
a second plurality of longitudinally oriented struts extending from the distally pointing vertices of the V-shaped elements, the longitudinally oriented struts being joined together near the radial center of the wire frame structure at a distal end of the embolic implant; and
a blood impermeable membrane covering at least a part of the wire frame structure extending from the proximal end of the wire frame structure to at least distal to the longitudinal center of the wire frame structure; and
withdrawing the delivery catheter.

17. The method of claim 16, wherein withdrawing the delivery catheter releases the embolic implant from the delivery catheter.

18. The method of claim 16, further comprising releasing the embolic implant from a delivery member disposed within the delivery catheter.

19. The method of claim 18, wherein the embolic implant is attached to the delivery member via a detachment joint, and wherein releasing the embolic implant from the delivery member comprises controlling a device to deliver electric current to the detachment joint to sever the detachment joint and release the embolic implant from the delivery catheter.

20. The method of claim 16, further comprising:
drawing the embolic implant back into the delivery catheter; and
repositioning the embolic implant within the vasculature.

21. The method of claim 16, further comprising delivering a drug or therapeutic agent to the patient via the delivery member.

22. The method of claim 16, wherein the delivery catheter comprises a first catheter, the method further comprising delivering a drug or therapeutic agent to the patient via a second catheter.

* * * * *